(12) United States Patent
Takamori et al.

(10) Patent No.: US 9,854,976 B2
(45) Date of Patent: Jan. 2, 2018

(54) PULSE WAVE VELOCITY MEASUREMENT METHOD

(71) Applicants: FUJIFILM Corporation, Tokyo (JP); TOHOKU UNIVERSITY, Sendai-shi, Miyagi (JP); NATIONAL UNIVERSITY CORPORATION FUKUSHIMA UNIVERSITY, Fukushima-shi, Fukushima (JP)

(72) Inventors: Tetsuya Takamori, Ashigarakami-gun (JP); Makoto Yoshizawa, Sendai (JP); Noriyasu Homma, Sendai (JP); Norihiro Sugita, Sendai (JP); Makoto Abe, Sendai (JP); Akira Tanaka, Fukushima (JP)

(73) Assignees: FUJIFILM Corporation, Tokyo (JP); TOHOKU UNIVERSITY, Miyagi (JP); NATIONAL UNIVERSITY CORPORATION FUKUSHIMA UNIVERSITY, Fukushima-Shi (JP)

( * ) Notice: Subject to any disclaimer, the term of this patent is extended or adjusted under 35 U.S.C. 154(b) by 170 days.

(21) Appl. No.: 14/840,656

(22) Filed: Aug. 31, 2015

(65) Prior Publication Data

US 2015/0366456 A1    Dec. 24, 2015

Related U.S. Application Data

(63) Continuation of application No. PCT/JP2013/078523, filed on Oct. 22, 2013.

(30) Foreign Application Priority Data

Mar. 8, 2013  (JP) ................................. 2013-047014

(51) Int. Cl.
  *A61B 5/00*   (2006.01)
  *A61B 5/0205* (2006.01)
  *A61B 5/021*  (2006.01)

(52) U.S. Cl.
  CPC ........ *A61B 5/0077* (2013.01); *A61B 5/02055* (2013.01); *A61B 5/02125* (2013.01); *A61B 5/6898* (2013.01); *A61B 5/72* (2013.01)

(58) Field of Classification Search
  CPC .............. A61B 5/0077; A61B 5/02055; A61B 5/02125; A61B 5/6898; A61B 5/72
  See application file for complete search history.

(56) References Cited

U.S. PATENT DOCUMENTS

| 5,941,828 A | 8/1999 | Archibald et al. |
| 2003/0004420 A1 | 1/2003 | Narimatsu |

(Continued)

FOREIGN PATENT DOCUMENTS

| CN | 101317756 A | 12/2008 |
| CN | 101732040 A | 6/2010 |

(Continued)

OTHER PUBLICATIONS

International Preliminary Report on Patentability (PCT/IPEA/409), issued in PCT/JP2013/078523. (English Translation)

(Continued)

*Primary Examiner* — Catherine Voorhees
(74) *Attorney, Agent, or Firm* — Birch, Stewart, Kolasch & Birch, LLP

(57) ABSTRACT

The present invention provides a pulse wave velocity measurement method and system as well as an imaging device available for everyday use by general users at low cost with measurement accuracy less affected by posture or the like. The present invention simultaneously images different parts of a human body in a non-contact state by a single visible (Continued)

light camera and acquires continuous time series image data. Then, the present invention detects each pulse wave from the image data in the different parts of the human body based on a temporal change in pixel value of the different parts of the human body, and then calculates a pulse wave velocity of the human body based on a time difference between the pulse waves in the different parts of the human body.

17 Claims, 21 Drawing Sheets

(56) References Cited

U.S. PATENT DOCUMENTS

| | | | |
|---|---|---|---|
| 2008/0306372 | A1 | 12/2008 | Ohki et al. |
| 2010/0149344 | A1 | 6/2010 | Ferguson |
| 2010/0150409 | A1 | 6/2010 | Ferguson |
| 2011/0157552 | A1* | 6/2011 | Bublitz ............. A61B 3/1005 351/209 |
| 2013/0046192 | A1* | 2/2013 | Lin ................. A61B 5/02007 600/500 |
| 2014/0206965 | A1 | 7/2014 | De Haan et al. |
| 2015/0323311 | A1* | 11/2015 | Muijs ................ G01B 11/162 356/28.5 |

FOREIGN PATENT DOCUMENTS

| | | |
|---|---|---|
| JP | 2001-514916 A | 9/2001 |
| JP | 2003-10139 A | 1/2003 |
| JP | 2006-239114 A | 9/2006 |
| JP | 2007-133595 A | 5/2007 |
| JP | 2007-319246 A | 12/2007 |
| JP | 2008-301915 A | 12/2008 |
| JP | 2010-154529 A | 7/2010 |
| JP | 2010-264095 A | 11/2010 |
| JP | 2011-104208 A | 6/2011 |
| JP | 2012-73997 A | 4/2012 |
| TW | 201309263 A1 | 3/2013 |
| WO | WO 2013/030739 A1 | 3/2013 |

OTHER PUBLICATIONS

Chinese Office Action and Search Report for Chinese Application No. 201380074359.7, dated Jan. 3, 2017, with an English translation of the Office Action only.
International Preliminary Report on Patentability (PCT/IPEA/409), issued in PCT/JP2013/078523, dated Mar. 24, 2014.
International Search Report, issued in PCT/JP2013/078523, dated Nov. 26, 2013.
Nishidate et al., "Non-contact measurements of plethysmogram by use of skin RGB images", The Institute of Electrical Engineers of Japan Kenkyukai Shiryo Hikari Ryoshi Device Kenkyukai OQD-11-030-037, Sep. 26, 2011, pp. 11-15.
Written Opinion of the International Searching Authority, issued in PCT/JP2013/078523, dated Nov. 26, 2013.
Chinese Office Action, dated May 31, 2017, for Chinese Application No. 201380074359.7 is provided, as well as an English translation.
Chinese Decision of Rejection for Chinese Application No. 201380074359.7, dated Aug. 23, 2017, with an English translation.

* cited by examiner

FIG.10
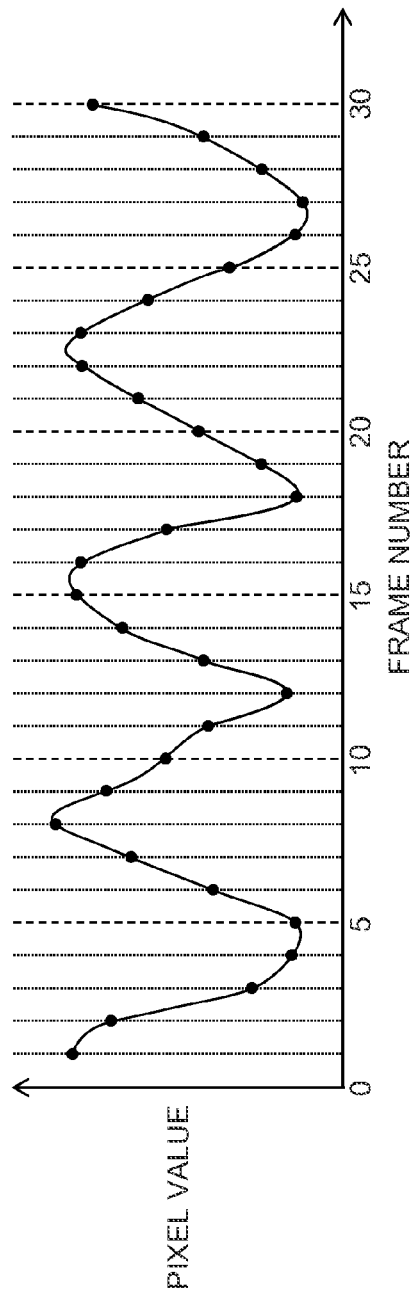
(A) FIRST SITE: CHEEK REGION
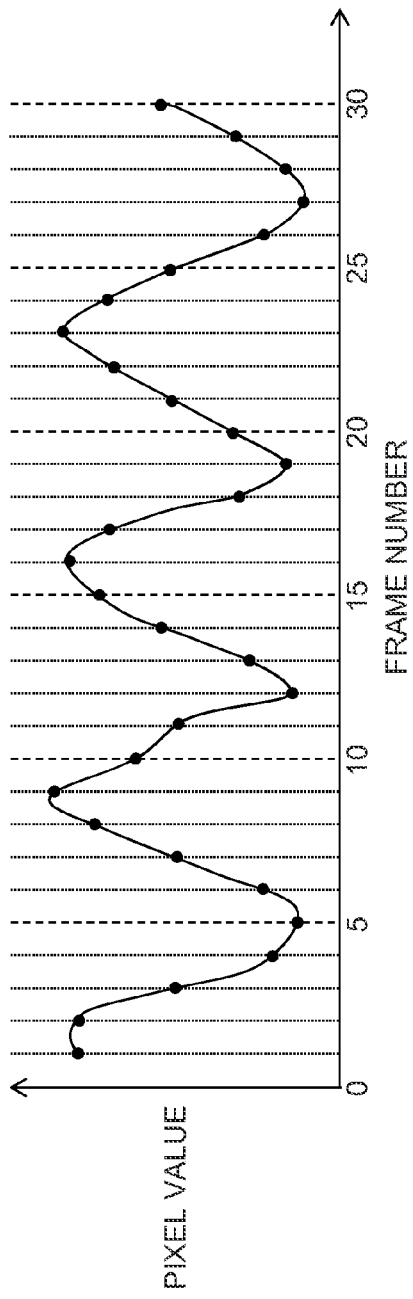
(B) SECOND SITE: PALM REGION

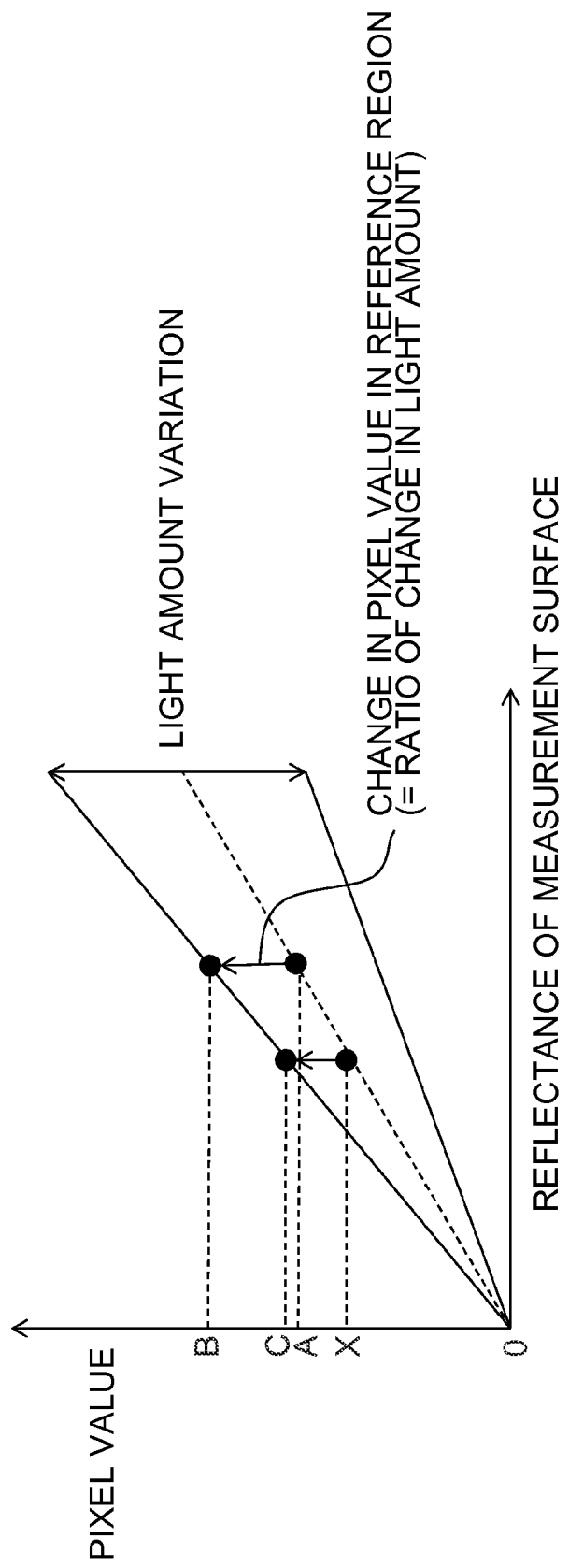

PULSE WAVE VELOCITY MEASUREMENT METHOD

CROSS-REFERENCE TO RELATED APPLICATIONS

This application is a Continuation of PCT International Application No. PCT/JP2013/078523 filed on Oct. 22, 2013, which claims priority under 35 U.S.C §119(a) to Japanese Patent Application No. 2013-047014 filed on Mar. 8, 2013. Each of the above application(s) is hereby expressly incorporated by reference, in its entirety, into the present application.

BACKGROUND OF THE INVENTION

Field of the Invention

The present invention relates to a pulse wave velocity measurement method and system as well as an imaging device, and more particularly to a technique for measuring a pulse wave velocity of a human body based on a time difference between pulse waves in different parts of a human body.

Description of the Related Art

A pulse wave velocity (PWV) has conventionally been used as one of the evaluation indexes in the circulatory system such as arteriosclerosis. Examples of pulse wave velocity measurement methods in practical use include a method of calculating a pulse wave velocity based on a time difference between pulse waves (pulse wave propagation time) measured in different parts of a human body and a distance between the parts measured at two points. In addition, there has been disclosed a technique for calculating blood pressure based on a time difference between pulse waves (pulse wave propagation time) measured at two points: wrist and finger, using a correlation between pulse wave velocity and blood pressure (see Japanese Patent Application Laid-Open No. 2011-104208; PTL 1).

These pulse wave velocity measuring devices are, however, not suitable for everyday use because these devices require a measurement sensor to be attached to two parts such as a pair of a neck region and a thigh region and a pair of an upper arm and an ankle joint, each pair being far away from each other. These devices may be available for everyday use by general users as long as the pulse wave sensors are attached to relatively easily attachable parts such as wrist and finger, but involve problems of requiring high time resolution, increasing cost, increasing measurement error depending on the condition of the joints, and the like.

In addition, there has been disclosed a method of measuring based on a time difference between an incident wave component and a reflected wave component contained in a pulse wave measured at one point of parts of a living body (see Japanese Patent Application Laid-Open No. 2003-10139; PTL 2). According to this, the pulse wave sensors can be relatively easily attached and may be used for everyday use by general users. However, the reflected wave component contained in the pulse wave is greatly affected by a change in blood vessel condition due to a change in posture or the like, thus causing a problem of being difficult to accurately measure.

Meanwhile, Japanese Patent Application Laid-Open No. 2007-319246 (PTL 3) discloses a technique in which a camera mobile phone is used to image a hand finger in a state of being in contact with an opening of the camera and to detect a temporal variation in the finger image, thereby to measure the pulse rate.

In addition, Japanese Patent Application Laid-Open No. 2010-264095 (PTL 4) discloses a technique in which an infrared camera is used to detect a temperature of a surface (skin) of a living body and to extract frequency data corresponding to a frequency component of a frequency band corresponding to a heart rate of a living body from a temporal variation in temperature information about the living body, and then based on the frequency data, the heart rate of the living body is measured.

SUMMARY OF THE INVENTION

However, the technique disclosed in PTL 3 assumes that for the purpose of measuring the pulse rate of a living body, the pulse rate is measured based on image data (finger image data) obtained by imaging one point of the living body in a state in which the hand finger is in contact with an opening of the camera, and thus the technique has a problem of being difficult to provide various functions by simultaneously imaging two different points in the living body.

In addition, the technique disclosed in PTL 4 requires an infrared camera to be used to acquire temperature information and hence an electronic device (such as a mobile phone) available for everyday use by general users cannot be used, thus causing problems such as increasing cost and being difficult to be widely used for general users. Note that PTL 4 also discloses a technique in which a visible light camera is used to determine a part of the user and then an infrared camera is used to acquire temperature information of the part. The technique, however, requires using both a visible light camera and an infrared camera, and hence it is considered to increase cost and to be difficult to be widely used for general users.

In view of such circumstances, the present invention has been made, and an object of the present invention is to provide a pulse wave velocity measurement method and system as well as an imaging device available for everyday use by general users at low cost with measurement accuracy less affected by posture or the like.

A pulse wave velocity measurement method according to a first aspect of the present invention comprises: an imaging step of simultaneously imaging different parts of a human body in a non-contact state by a single visible light camera and generating continuous time series image data; a pulse wave detection step of detecting each pulse wave in the different parts of the human body from the image data based on a temporal change in pixel value of the different parts of the human body; and a pulse wave velocity calculation step of calculating a pulse wave velocity of the human body based on a time difference between pulse waves in the different parts of the human body.

A pulse wave velocity measurement method according to a second aspect of the present invention comprises: an imaging step of simultaneously imaging different parts of a human body in a non-contact state by a single visible light camera and generating continuous time series image data; an optical information detection step of detecting temporal variation information about at least one of a light amount and a color of illumination light emitted to the different parts of the human body from the image data based on a temporal change in pixel value at a reference position other than the different parts of the human body; a correction step of correcting the image data so as to cancel an effect due to the temporal variation in the light amount or the color of the illumination light based on the variation information detected by the optical information detection step; a pulse wave detection step of detecting each pulse wave in the different parts of the human body from the image data corrected by the correction step based on the temporal change in pixel value of the different parts of the human body; and a pulse wave velocity calculation step of calculating a pulse wave velocity of the human body based on a time difference between pulse waves in the different parts of the human body.

A pulse wave velocity measurement method according to a third aspect of the present invention comprises: an imaging step of simultaneously imaging different parts of a human body in a non-contact state by a single visible light camera and generating continuous time series image data; an interpolation step of generating interpolation data obtained by temporally interpolating a temporal change in pixel value of the different parts of the human body from the image data; a pulse wave detection step of detecting each pulse wave in the different parts of the human body based on the interpolation data; and a pulse wave velocity calculation step of calculating a pulse wave velocity of the human body based on a time difference between pulse waves in the different parts of the human body.

A pulse wave velocity measurement system according to a fourth aspect of the present invention comprises: an imaging unit that simultaneously images different parts of a human body in a non-contact state by a single visible light camera and generates continuous time series image data; a pulse wave detection unit that detects each pulse wave in the different parts of the human body from the image data based on a temporal change in pixel value of the different parts of the human body; and a pulse wave velocity calculation unit that calculates a pulse wave velocity of the human body based on a time difference between pulse waves in the different parts of the human body.

An imaging device according to a fifth aspect of the present invention comprises: an imaging unit that simultaneously images different parts of a human body in a non-contact state by a single visible light camera and generates continuous time series image data; and a tracking processing unit that performs tracking processing on the different parts of the human body by setting a region containing the different parts of the human body in a first image of a plurality of images constituting the image data as a tracking region, extracting a feature quantity from an image in the tracking region, and detecting an image region having the highest degree of similarity to the feature quantity in a second image chronologically following the first image as a region containing the different parts of the human body.

An imaging device according to a sixth aspect of the present invention comprises: an imaging unit that simultaneously images different parts of a human body in a non-contact state by a single visible light camera and generates continuous time series image data; and a guide frame display unit that displays an imaging guide frame corresponding to the different parts of the human body on a screen displaying the image imaged by the imaging unit.

The present invention can measure a pulse wave velocity from a temporal variation in pixel value of different parts of a human body based on image data obtained by simultaneously imaging the different parts of the human body in a non-contact state by a single visible light camera, and hence can be used for everyday use by general users at low cost without being affected by posture or the like and can improve measurement accuracy in the pulse wave velocity.

BRIEF DESCRIPTION OF THE DRAWINGS

FIG. 10 is a graph illustrating changes in pixel value of first and second measurement sites.

FIG. 22 is a graph illustrating a relation between the light amount of illumination light and the pixel value.

DETAILED DESCRIPTION OF THE PREFERRED EMBODIMENTS

Hereinafter, preferable embodiments of the present invention will be described in detail with reference to the accompanying drawings.

First Embodiment

First, the description focuses on the outline of a pulse wave velocity system according to a first embodiment of the present invention.

Figure 1:
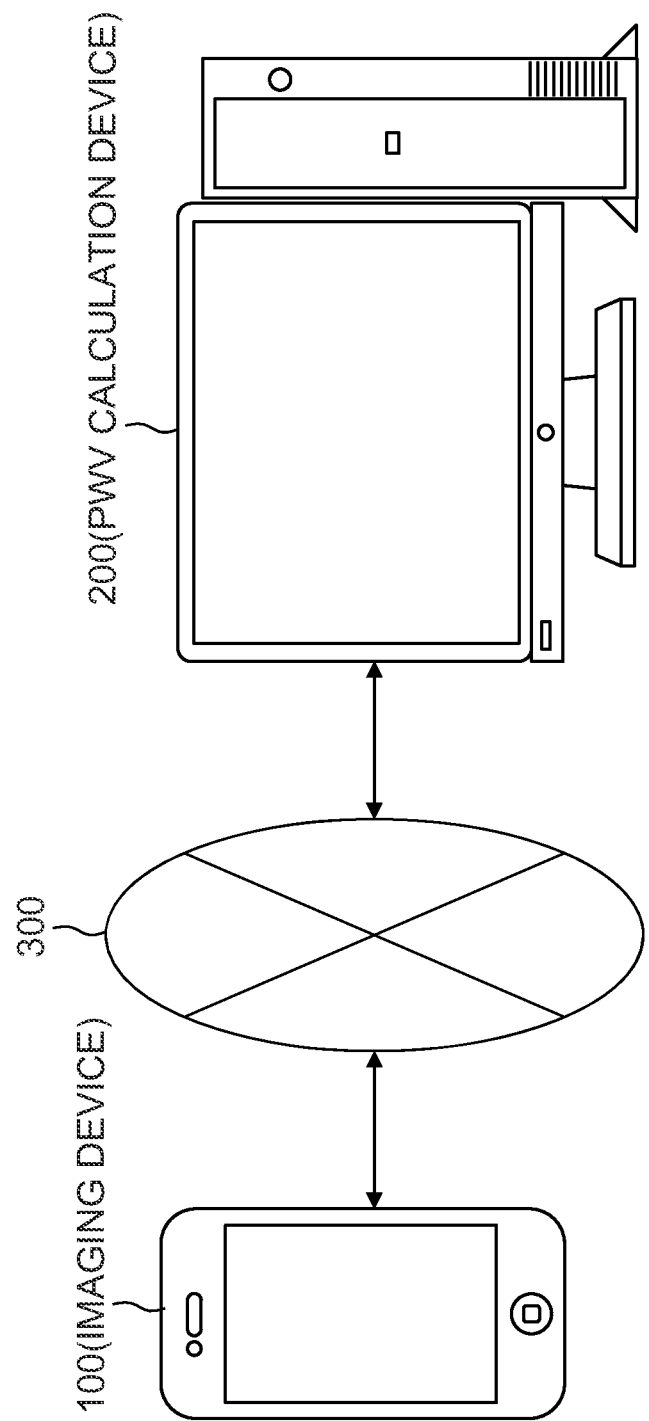
FIG. 1 is a schematic view illustrating an entire configuration of a pulse wave velocity measurement system according to a first embodiment.

FIG. 1 is a schematic view illustrating an entire configuration of the pulse wave velocity measurement system according to the present embodiment. As illustrated in FIG. 1, the pulse wave velocity measurement system of the present embodiment includes an imaging device 100 and a pulse wave velocity calculation device (hereinafter referred to as "a PWV calculation device") 200. The imaging device 100 and the PWV calculation device 200 are connected to each other so that various data can be transmitted and received through a network 300 such as the Internet.

The imaging device 100 is constituted by a terminal device having a typical imaging function (visible light camera) such as a smartphone, a camera mobile phone, a digital camera, a video camera, and a Web camera. The present embodiment assumes that the imaging device 100 is a smartphone. The imaging device 100 images two different parts (hereinafter also referred to as "measurement sites") of a human body in a non-contact state and outputs continuous time series image data (RGB format image data). The image data is not limited to moving image data, but may be a plurality of still image data. The present embodiment assumes that the image data is constituted by moving image data including a plurality of frame images as an example.

The measurement sites to be imaged by the imaging device 100 are not limited to any particular sites as long as the sites are far away from each other in a skin region of the human body, but in view of convenience of general users, a face region and a hand region are preferable, and particularly among them, a cheek region and a palm region are more preferable. The skin region of the human body changes in blood flow rate according to pulse wave (pulsation), and hence the PWV calculation device 200 to be described later can acquire a pulse wave signal (pulse wave data) whose amplitude changes according to the pulse wave by detecting a temporal variation in pixel value in the skin region (color change in the skin). Note that the cheek region and the palm region have a wider skin region than other regions in the face region and the hand region, and thus allow the color change in the skin to be reliably detected in a state of suppressing the effect of noise as much as possible.

The PWV calculation device 200 is constituted by a common personal computer, and is installed, for example, in a medical facility such as a hospital. Based on image data containing two different parts (measurement sites) of the human body imaged by the imaging device 100, the PWV calculation device 200 detects a change in pixel value in each measurement site, thereby to acquire a pulse wave signal (pulse wave data) whose amplitude changes according to the pulse wave. Then, the PWV calculation device 200 calculates the pulse wave velocity from a time difference between pulse wave signals in each measurement site and outputs the results on a display unit such as a monitor. Note that in order to detect the change in pixel value in each measurement site, the temporal variation in pixel value of an R component, a G component or a B component of each color component of an RGB image may be detected.

According to the pulse wave velocity measurement system of the present embodiment, the imaging device 100 is constituted by a smartphone, a camera mobile phone, a digital camera, a video camera, or the like, to measure the pulse wave velocity using the image data obtained by imaging the two different parts (measurement sites) of the human body in a non-contact state. Thus, the pulse wave velocity measurement system can be easily used for everyday use by general users at low cost without being affected by posture or the like, thus allowing highly accurate measurement. The following description focuses on the configuration of each component of the pulse wave velocity measurement system.

Figure 2:
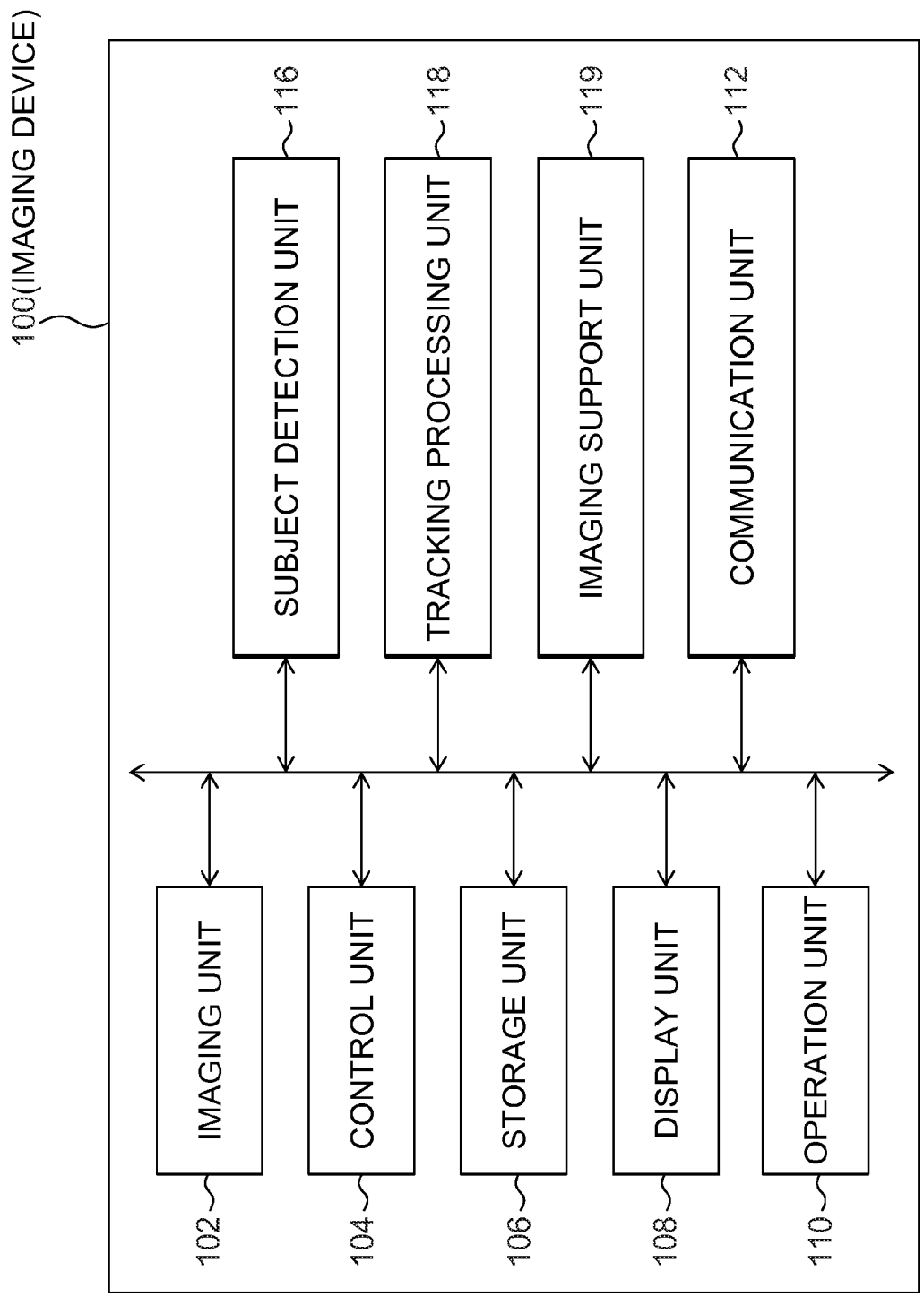
FIG. 2 is a block diagram illustrating a configuration of an imaging device.

FIG. 2 is a block diagram illustrating the configuration of the imaging device 100. As illustrated in FIG. 2, the imaging device 100 includes an imaging unit 102, a control unit 104, a storage unit 106, a display unit 108, an operation unit 110, a communication unit 112, a subject detection unit 116, a tracking processing unit 118, and an imaging support unit 119.

The imaging unit 102 includes an imaging lens and a visible light imaging element (such as a CCD—Charge Coupled Device sensor and a CMOS—Complementary MOS sensor) for receiving visible light, wherein the imaging element captures a subject image through the imaging lens and converts the subject image into an electrical signal as image data. The imaging unit 102 further performs, on the image data, signal processing such as noise reduction processing, black level subtraction processing, color mixing correction, shading correction, white balance correction, gamma correction, synchronization processing, and RGB/YC conversion processing. According to the present embodiment, the imaging unit 102 outputs RGB format image data.

The display unit 108 is a display (such as a touch panel display) composed of a liquid crystal, an organic EL, and the like. The display unit 108 displays the image data acquired by the imaging unit 102, a graphical user interface (GUI) for operating the imaging device 100, and the like.

The communication unit 112 transmits and receives various data via a network such as the Internet to and from a communication unit 202 of a PWV calculation device 200 to be described later.

The storage unit 106 includes a read only memory (ROM), a random access memory (RAM), and the like. The storage unit 106 stores programs of the operating system and various application software executed by the control unit 104 as well as the image data acquired by the imaging unit 102.

The control unit 104 is constituted by, for example, a CPU, a microcomputer, and the like, and performs an overall operation control of the imaging device 100 by executing the programs of the operating system and the various application software stored in the storage unit 106.

Figure 3:
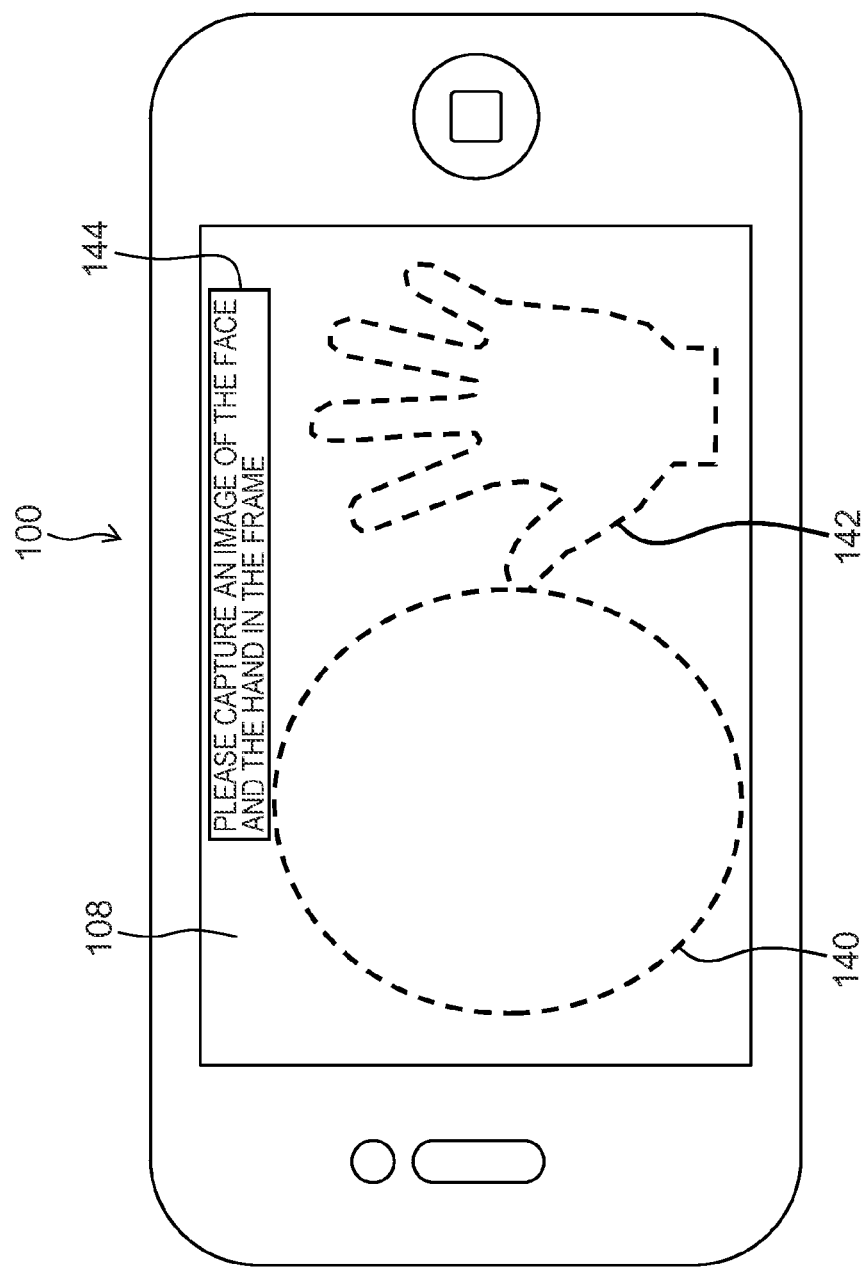
FIG. 3 is a view illustrating an example of an imaging guide frame at horizontal imaging.
Figure 4:
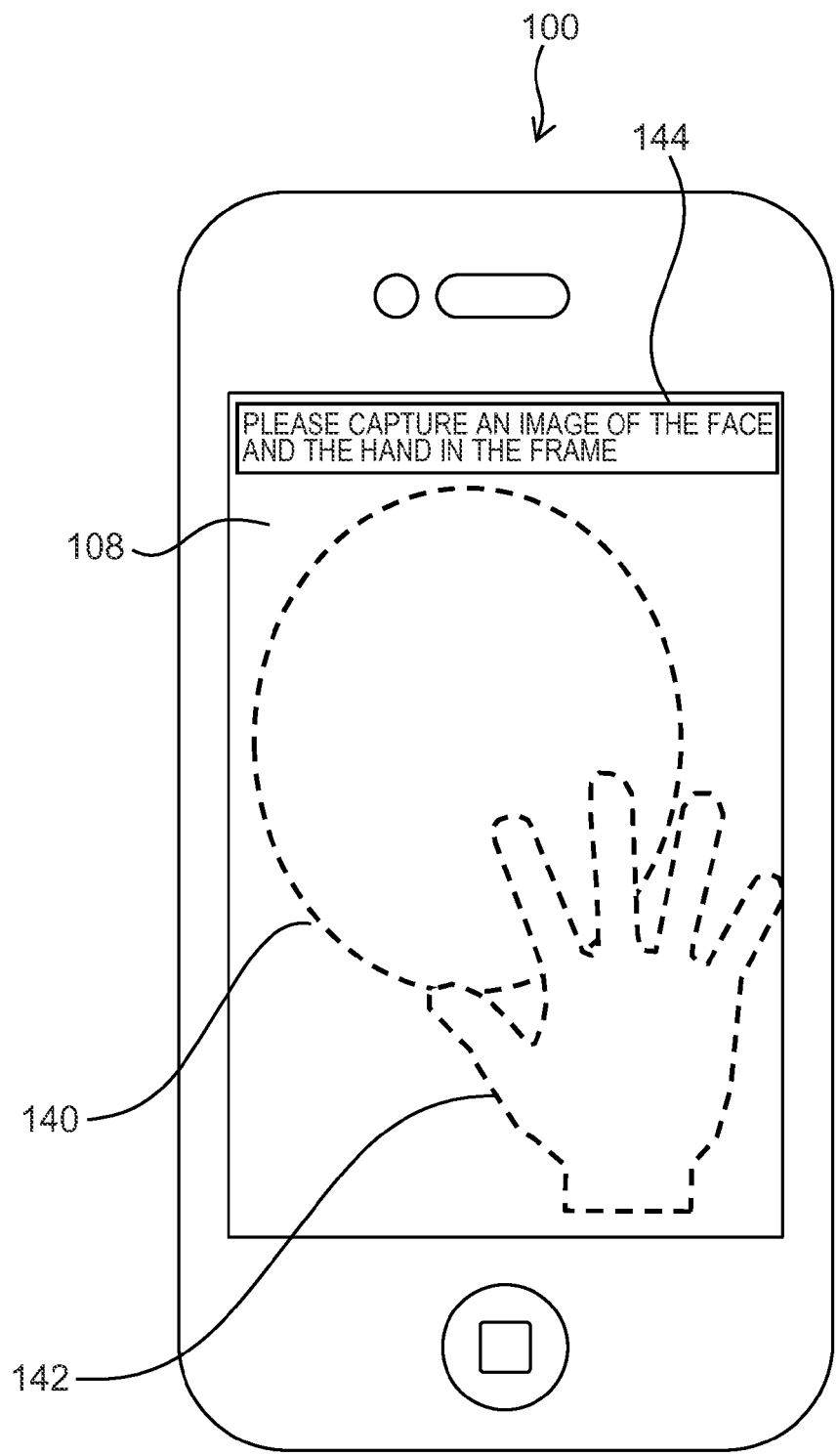
FIG. 4 is a view illustrating an example of an imaging guide frame at vertical imaging.
Figure 5:
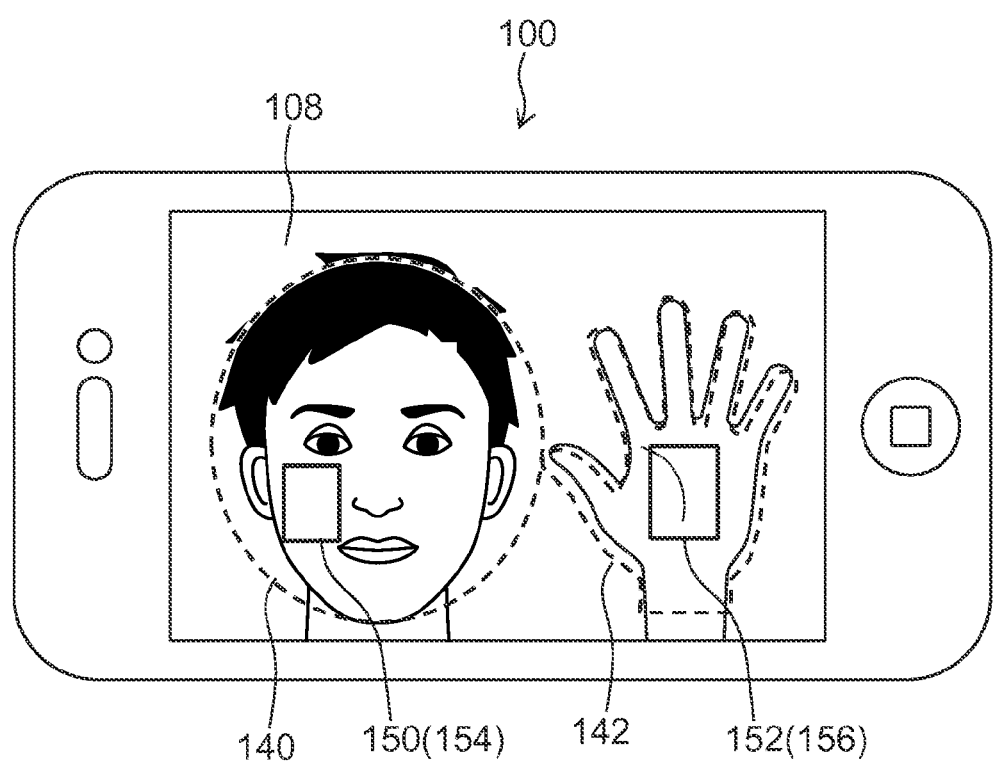
FIG. 5 is a view illustrating a state in which a face and a hand are imaged to overlap in the imaging guide frame.

The imaging support unit 119 (corresponding to "guide frame display unit" of the present invention) includes, for example, a CPU, a microcomputer, and the like, and displays an imaging guide frame combined with the captured image on a screen of the display unit 108. For example, as illustrated in FIGS. 3 and 4, when the imaging device 100 starts video imaging, a face guide frame 140 and a hand guide frame 142 are displayed as the imaging guide frame on the screen of the display unit 108. The imaging guide frame is not limited to any particular shape, and may be of various shapes. Note that a notification message 144 such as "Please capture an image of the face and the hand in the frame" is displayed in an upper portion of the screen of the display unit 108. Then, as illustrated in FIG. 5, the user tends to capture a video image of the face and the hand at a position and with a size fitted to the face guide frame 140 and the hand guide frame 142. Therefore, the image data of the face and hand captured at an appropriate position can be acquired and hence the pulse wave data at each measurement site can be obtained with a good accuracy.

Note that the user may selectively switch between display and non-display of imaging support functions such as the face guide frame 140, the hand guide frame 142, and the notification message 144. For example, FIG. 5 illustrates an example of non-display of the notification message 144.

The operation unit 110 includes a numeric keypad and buttons for selecting various functions, or a touch panel, and constitutes a GUI together with the display unit 108. The operation unit 110 is used for various operations such as an input operation for starting or ending the video recording.

The subject detection unit 116 detects two different parts (first and second measurement sites) of a human body as particular subject regions from a first inputted frame image (initial frame image) of the image data acquired by the imaging unit 102. The present embodiment detects a cheek region as the first measurement site and detects a palm region as the second measurement site. Examples of the method for detecting each measurement site may include a method using pattern matching, a method using a classifier obtained by learning using a large number of sample images of human faces and hands, and other methods. Alternatively, a specific face may be recognized by previously registering the human face in the ROM and performing face recognition after the object is detected. Note that as illustrated in FIG. 5, subject frames 150 and 152 are displayed in respective positions corresponding to respective measurement sites (that is, the cheek region and the palm region) detected as the subject regions on the screen of the display unit 108.

Figure 6:
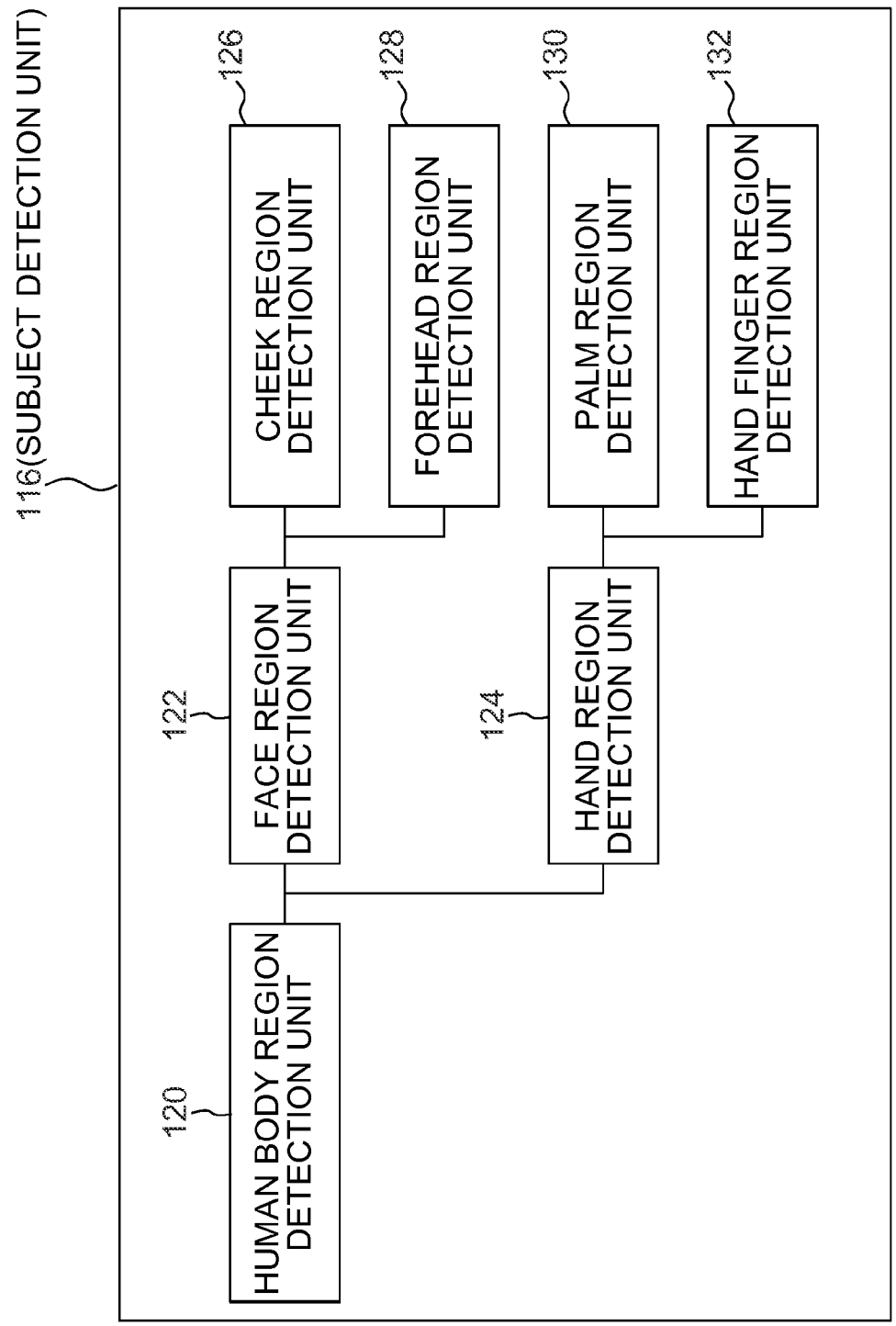
FIG. 6 is a block diagram illustrating a configuration of a subject detection unit.

FIG. 6 is a block diagram illustrating a configuration of the subject detection unit 116. As illustrated in FIG. 6, the subject detection unit 116 includes a human body region detection unit 120 detecting a human body region of the subject, a face region detection unit 122 detecting a face region from the human body region, and a hand region detection unit 124 detecting a hand region from the human body region. The subject detection unit 116 further includes a cheek region detection unit 126 detecting a cheek region from the face region, a forehead region detection unit 128 detecting a forehead region from the face region, a palm region detection unit 130 detecting a palm region from the hand region, and a hand finger region detection unit 132 detecting a hand finger region from the hand region. Such a configuration of the subject detection unit 116 allows each part to be detected stepwise in detail from the human body region.

Note that if a plurality of face regions and hand regions are detected, it is difficult to associate the face regions with the hand regions, and hence it is preferable to notify the user of an error message prompting to capture an image again. Note also that if one face region and two hand regions are detected, the regions are likely to belong to the same person, and hence in that case, the regions may be detected as the subject regions.

Referring back to FIG. 2, the tracking processing unit 118 performs tracking processing on the cheek region and the palm region, which are the first and second measurement sites detected by the subject detection unit 116, regarded as tracking regions. Specifically, a current frame image is searched for a region (corresponding to a tracking region in an original frame image) having a highest degree of similarity between the feature quantity of an image in a tracking region in a previous frame image and the feature quantity of an image in a tracking candidate region of the current frame image.

Examples of the information identifying the tracking region include information indicating the position of the tracking region, information indicating the color and intensity of the tracking region, and other information. When the current frame image is acquired from the storage unit 106, the tracking processing unit 118 detects a region having color and intensity similar to those of the tracking region in a predetermined region near the position of the tracking region identified by the previous frame image, from the current frame image, thereby to identify the tracking region. Then, the tracking processing unit 118 repeats a process of identifying the tracking region from the frame images sequentially stored in the storage unit 106, based on the position of the tracking region and the color and intensity of the tracking subject identified by the current frame image. The tracking processing unit 118 performs the tracking processing in this manner to adjust various imaging parameters (focus, brightness, and the like) so as to be best suited for imaging each measurement site (first and second measurement sites) as the tracking regions.

Figure 7:
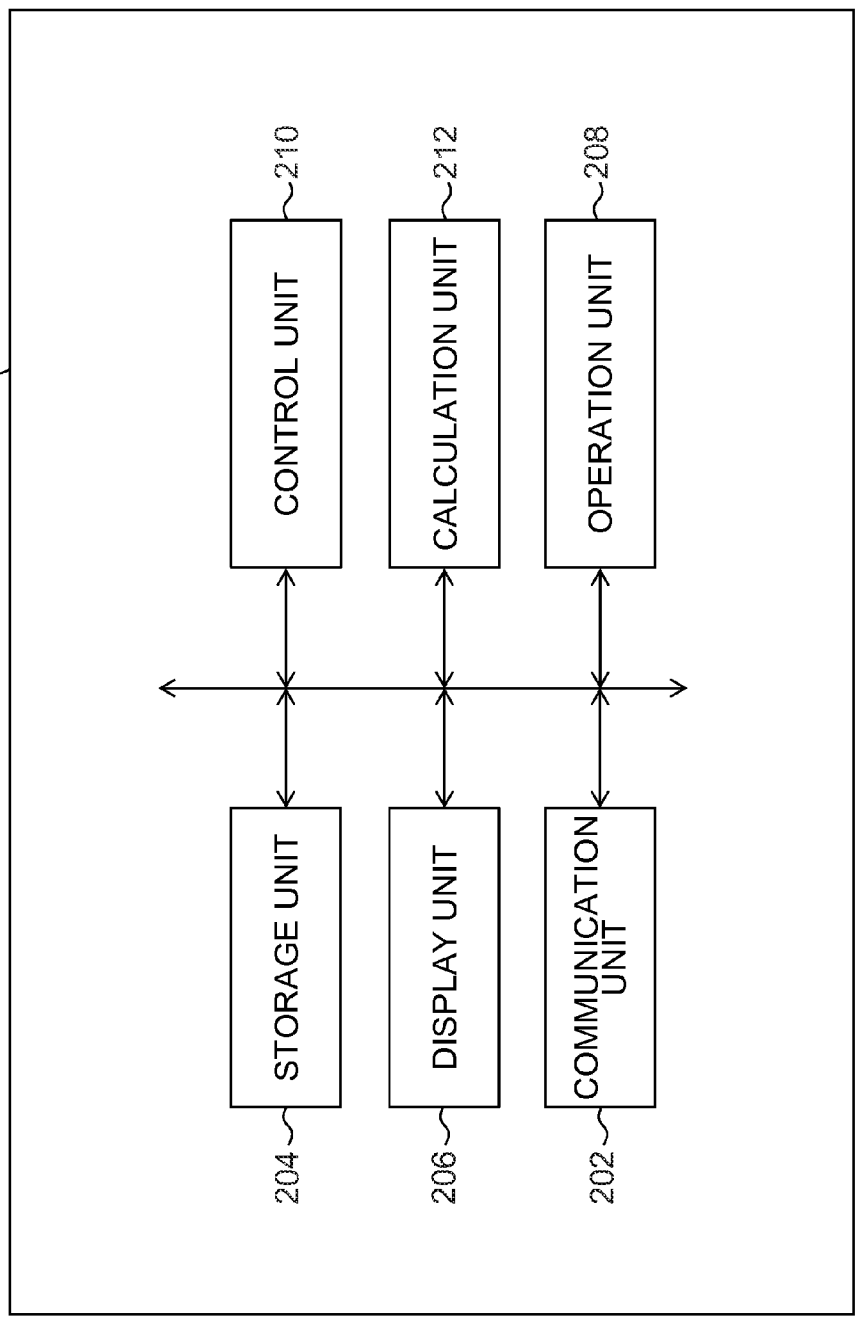
FIG. 7 is a block diagram illustrating a configuration of a pulse wave velocity calculation device.

FIG. 7 is a block diagram illustrating a configuration of the PWV calculation device 200. As illustrated in FIG. 7, the PWV calculation device 200 includes a communication unit 202, a storage unit 204, a display unit 206, an operation unit 208, a control unit 210, and a calculation unit 212. Note that the PWV calculation device 200 is not limited to be physically constituted by a single computer, but may be constituted by a plurality of computers connected to each other via a network.

The storage unit 204 is constituted by, for example, a ROM, a RAM, or a hard disk drive (HDD), and stores programs of the operating system and various application software executed by the control unit 210. The storage unit 204 also functions as an image memory for temporarily storing the image data acquired from the imaging device 100.

The display unit 206 is constituted by a display such as a liquid crystal monitor or the like enabling color display, and displays various management information outputted from the control unit 210.

The operation unit 208 includes a mouse, a keyboard, and the like. The results operated by the operation unit 208 are inputted to the control unit 210 which detects whether or not an input is made, on which button the input is made, and the like.

The communication unit 202 transmits and receives data via a network such as the Internet to and from the communication unit 112 of the imaging device 100.

The control unit 210 is constituted by, for example, a CPU, a microcomputer, and the like, and performs an overall operation control of the PWV calculation device 200 by executing the programs of the operating system and the various application software stored in the storage unit 204.

The calculation unit 212 is constituted by, for example, a CPU, a microcomputer, and the like, and performs various calculation processes according to instructions from the control unit 210.

Figure 8:
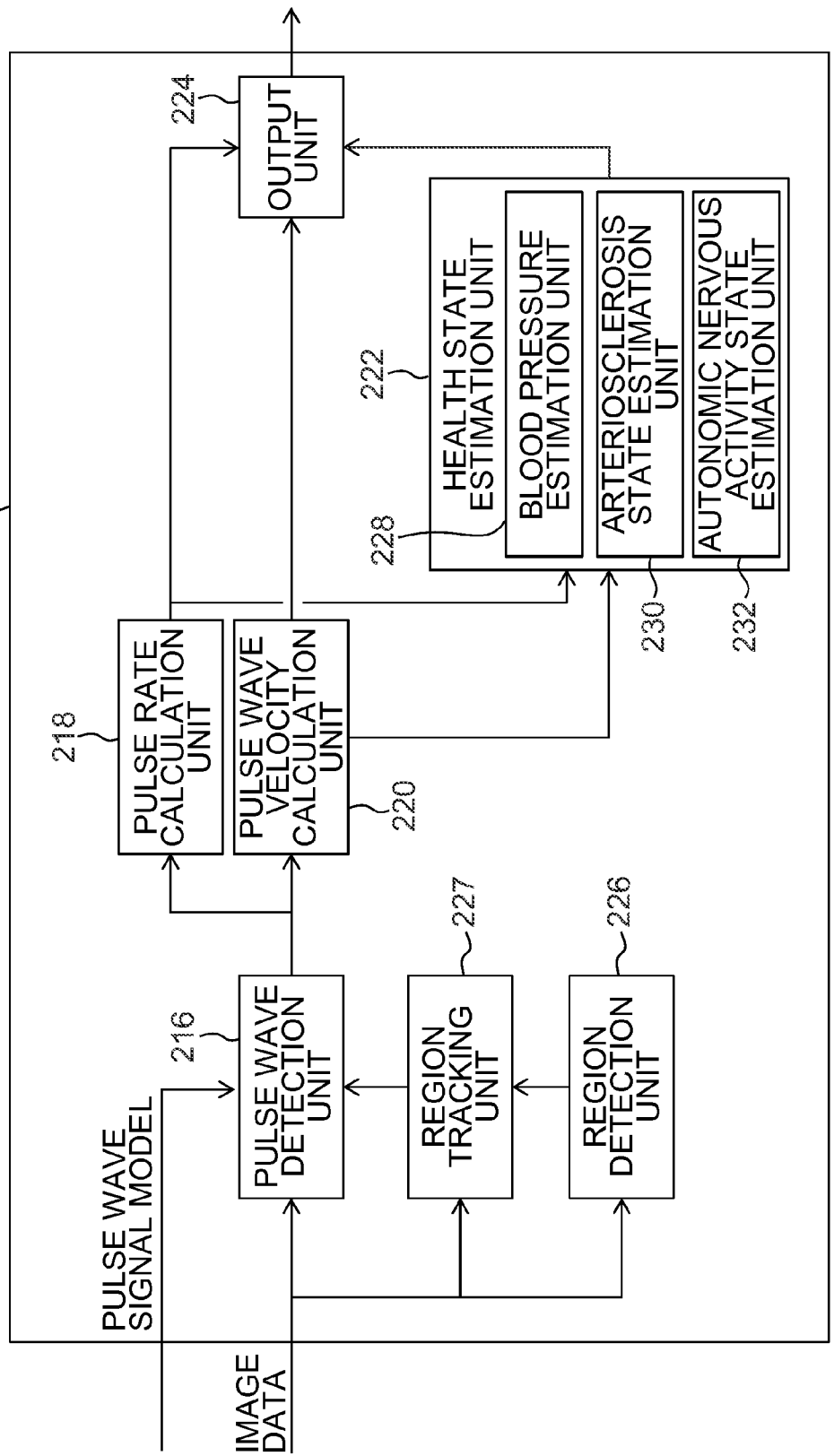
FIG. 8 is a block diagram illustrating a configuration of a calculation unit.

FIG. 8 is a block diagram illustrating a configuration of the calculation unit 212. As illustrated in FIG. 8, the calculation unit 212 includes a region detection unit 226, a region tracking unit 227, a pulse wave detection unit 216, a pulse rate calculation unit 218, a pulse wave velocity calculation unit 220, a health state estimation unit 222, and an output unit 224.

The region detection unit 226 and the region tracking unit 227 are functional blocks for extracting the first and second measurement sites from each frame image of the image data and perform processes similar to those of the subject detection unit 116 and the tracking processing unit 118 of the imaging device 100. More specifically, for example, the region detection unit 226 detects a cheek region and a palm region as the first and second measurement sites from the first inputted frame image (initial frame image), and then the region tracking unit 227 considers these regions as the tracking regions to perform tracking processing on a frame image following this frame image. The tracking processing result (tracking information) is outputted to the pulse wave detection unit 216. Note that if the tracking processing result (tracking information) by the tracking processing unit 118 of the imaging device 100 can be acquired, the PWV calculation device 200 can use the tracking information. In this case, the calculation unit 212 may omit the region detection unit 226 and the region tracking unit 227.

Figure 9:
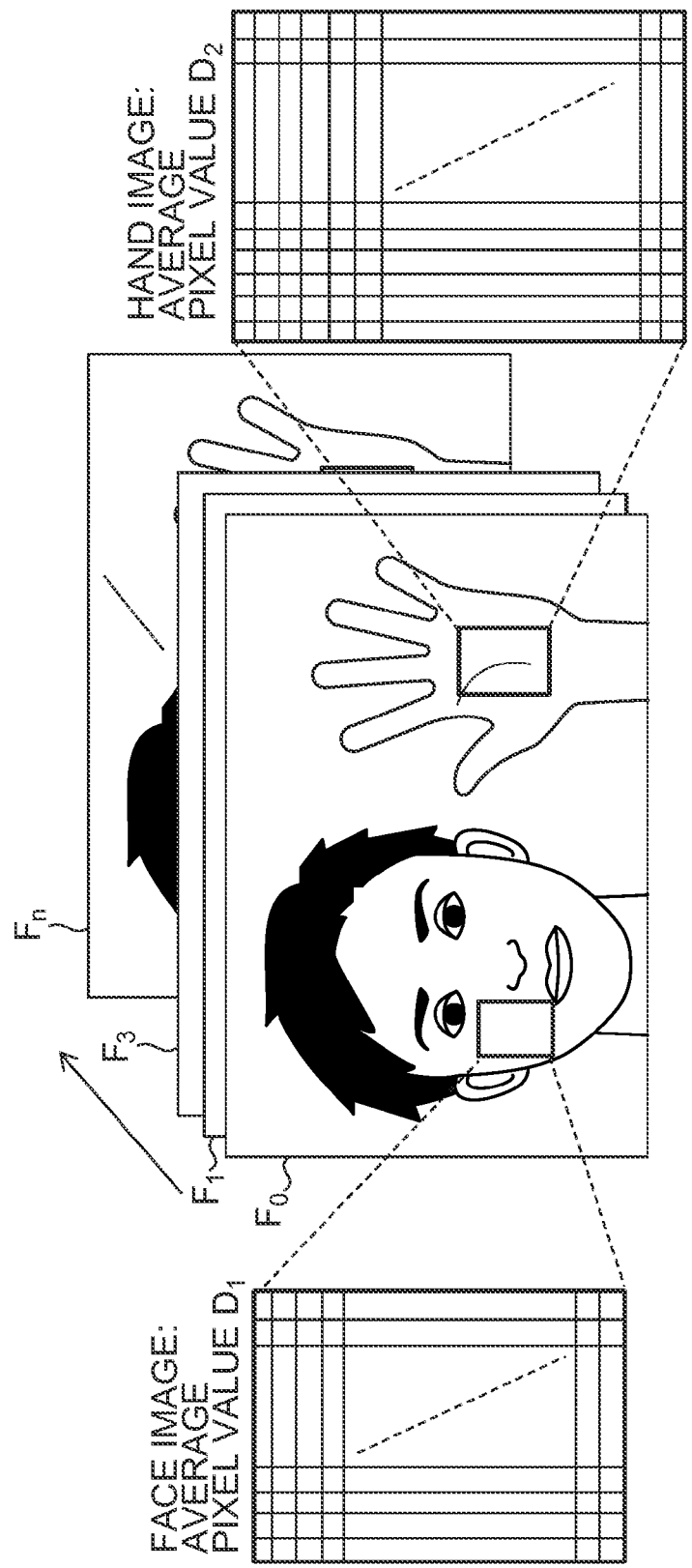
FIG. 9 is an explanatory drawing for describing processing to be performed by a pulse wave detection unit.

Based on the tracking information acquired from the region tracking unit 227 or the tracking processing unit 118 of the imaging device 100, the pulse wave detection unit 216 extracts each measurement site from each frame image and detects a change in pixel value in each measurement site. More specifically, for example, as illustrated in FIG. 9, the pulse wave detection unit 216 calculates an average pixel value D1 of pixel values of each pixel belonging to the cheek region (first measurement site) and an average pixel value D2 of pixel values of each pixel belonging to the palm region (second measurement site) for each frame image $F_0$ to $F_n$. Thus, for example, a graph indicating a change in pixel value as illustrated in FIG. 10 is obtained. Note that in FIG. 10, the horizontal axis indicates frame numbers (time axis), and the vertical axis indicates pixel values (average value). Note also that the waveform illustrated by a solid line in FIG. 10 is calculated from the pixel values (black circle portions) in each measurement site in each frame image. This waveform is a pulse wave signal (pulse wave data) having an amplitude corresponding to the pulse wave.

By the way, when the pulse wave signal is obtained from the pixel values (black circle portions in FIG. 10) of each frame image, the pulse wave signal can be obtained with a high time resolution as long as the frame rate is high. A camera used by general users on a daily basis has a frame rate equal to or less than 30 fps, and hence it is considered that it may be difficult to estimate an autonomic nervous state requiring a time resolution of a few milliseconds. Note that a time resolution of approximately 100 milliseconds is sufficient to measure only blood pressure and pulse rate.

Figure 11:
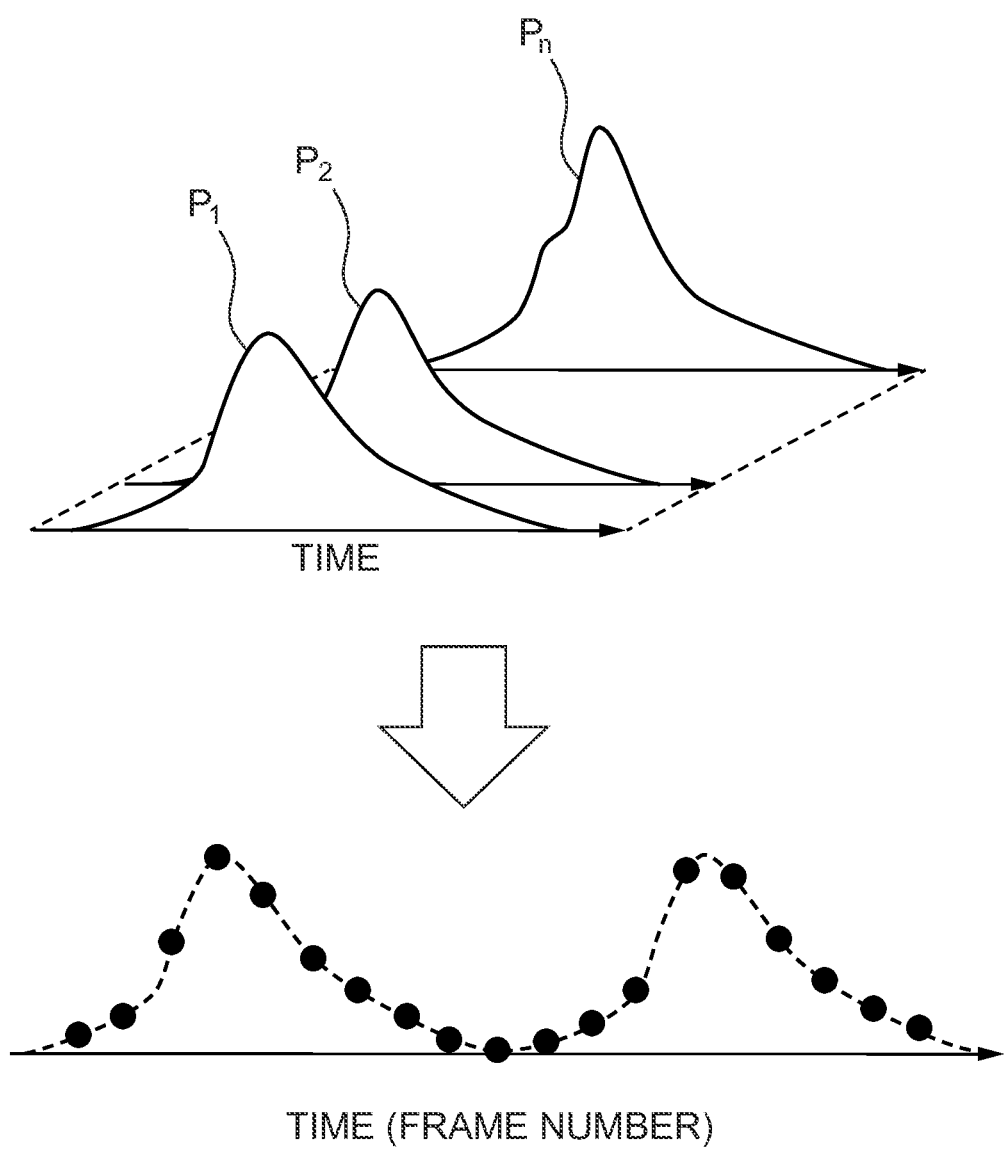
FIG. 11 is an explanatory drawing for describing a pulse wave signal model.

Thus, in the present embodiment, in order to enable the pulse wave signal to be obtained with a high time resolution even if the image data has a frame rate equal to or less than 30 fps, for example, a plurality of pulse wave signal models (waveform models) $P_1$ to $P_n$ as illustrated in FIG. 11 are previously stored in the storage unit 204. Then, each pulse wave signal model $P_1$ to $P_n$ is configured to be transferred from the storage unit 204 to the pulse wave detection unit 216 (see FIG. 8). Note that the each pulse wave signal model $P_1$ to $P_n$ includes a plurality of mutually different waveform patterns (pulse waveforms).

As an "interpolation step" of the present invention, the pulse wave detection unit 216 performs fitting on each measured data (pixel value of each frame image) for each pulse wave signal model $P_1$ to $P_n$, and selects a pulse wave signal model having the highest degree of similarity from them. Then, the pulse wave detection unit 216 uses the selected pulse wave signal model to estimate an unacquired change in pixel value between the frame images. Therefore, even if the image data has a frame rate equal to or less than 30 fps, an unacquired change in pixel value between the frame images can be estimated based on the pulse wave signal model, and hence the pulse wave signal as illustrated in FIG. 10 can be obtained with a high time resolution and a good accuracy.

Figure 12:
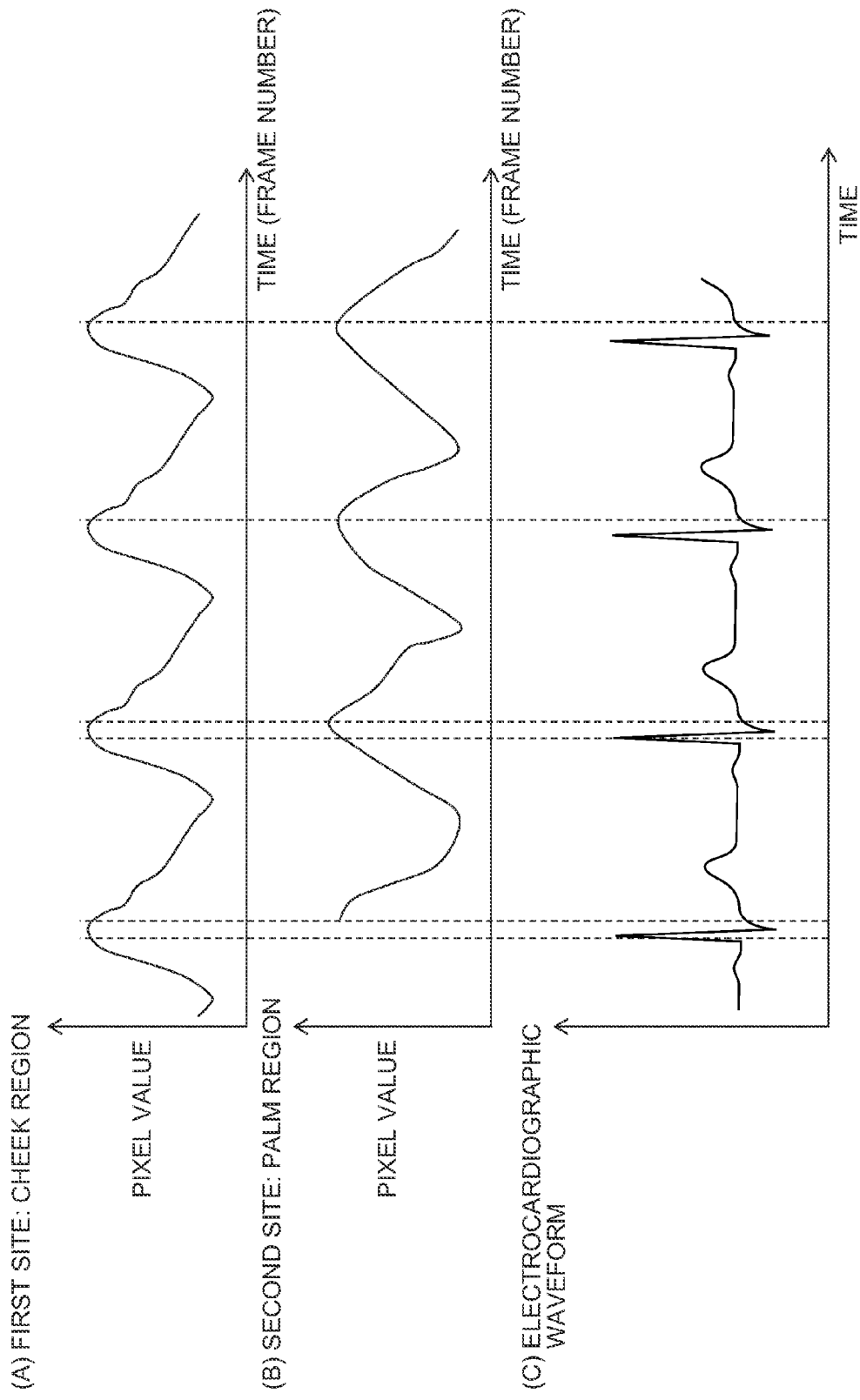
FIG. 12 is a graph illustrating a relationship between a change in pixel value of the first and second measurement sites and an electrocardiographic waveform.

FIG. 12 is a graph illustrating a relationship between a change in pixel value of the first and second measurement sites and an electrocardiographic waveform. As illustrated in FIG. 12, the change in pixel value in each measurement site has a correlation with the electrocardiographic waveform, and hence the change in pixel value in each measurement site can be used as a pulse wave signal (pulse wave data) whose amplitude changes according to the pulse wave (pulsation). This is because the blood flow rate in a skin region of the face and the hand of a human body changes according to the heart rate, and the pixel value in each measurement site changes in amplitude according to the pulse wave (pulsation). Therefore, a change in pixel value of a face region and a hand region (preferably a cheek region and a palm region) of the human body as the skin region is detected and the change can be used as the pulse wave signal (pulse wave data) whose amplitude changes according to the pulse wave. Thus detected pulse wave signal of each measurement site is outputted to the pulse rate calculation unit 218 and the pulse wave velocity calculation unit (hereinafter referred to as a PWV calculation unit) 220.

In the present embodiment, it is preferable that filtering processing using a spatial filter is performed on the image data before the pixel value in each measurement site is calculated. Specifically, after the first and second measurement sites are extracted from each frame image, the pixel value of a pixel of interest is converted using the pixel values of the pixel of interest and its surrounding pixels (M×N pixels) for all pixels belonging to each measurement site. As the spatial filter, a smoothing filter (such as an averaging filter), a median filter, or a combination of these filters can be preferably used. Examples of the filer size may include 3×3, 5×5, 7×7 pixels, which may be determined according to the amount of change in pixel value.

Performing filtering processing using a spatial filter on the image data in this manner allows a change in pixel value in each measurement site to be detected with a good accuracy without being affected by noise due to variations in skin color, electrical noise, how the light is incident, movement of the human body, movement of the camera, detection error of each measurement site, and the like. Note that after the noise reduction processing is performed on the image data, a noise component may still remain in the pulse wave signal as a time signal. In this case, noise reduction processing using a frequency smoothing filter, a trimmed mean filter, a median filter, or the like may be performed on the pulse wave signal.

Alternatively, filtering processing using a two-dimensional spatial frequency filter instead of the spatial filter or with a combination of the spatial filter may be performed. The filtering processing can remove an unwanted frequency noise component from the image data. Alternatively, outlier processing may be performed.

Referring back to FIG. 8, the pulse rate calculation unit 218 calculates the pulse rate of each measurement site based on the pulse wave signal of each measurement site detected by the pulse wave detection unit 216, and outputs the result to the health state estimation unit 222 and the output unit 224.

Figure 13:
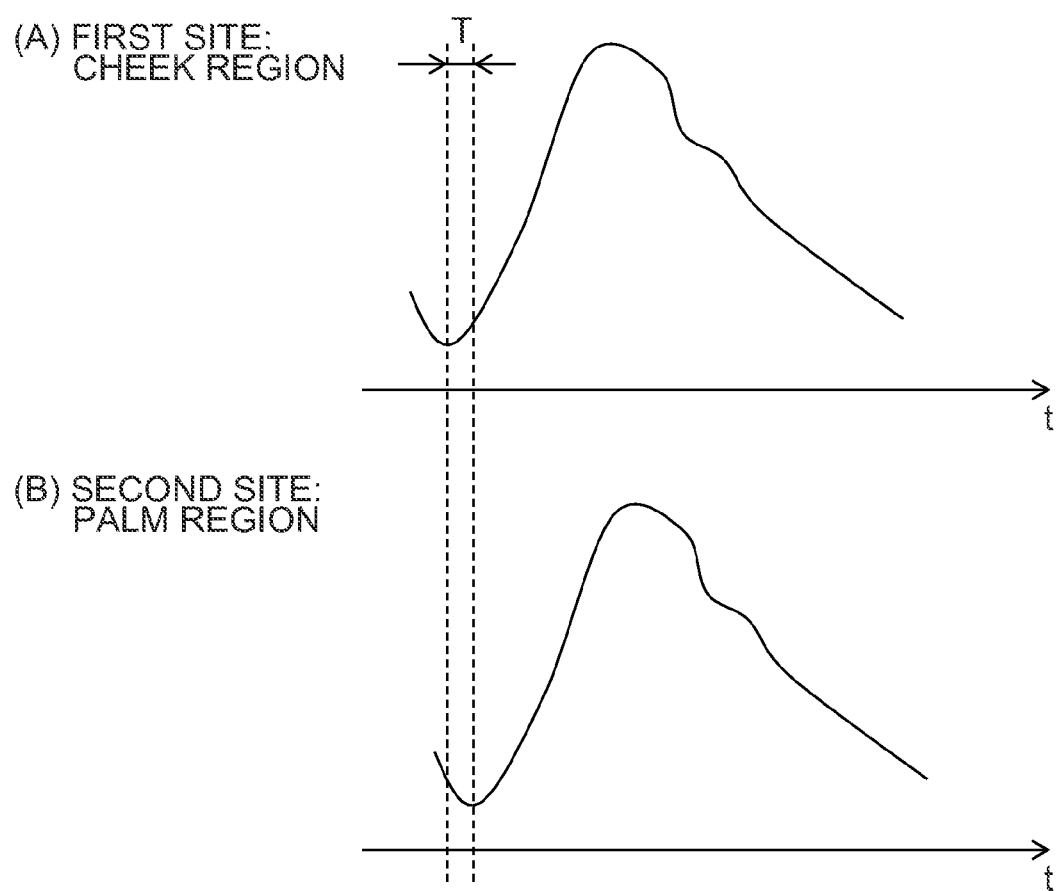
FIG. 13 is an explanatory drawing for describing a method of calculating a pulse wave velocity.

The PWV calculation unit 220 calculates the pulse wave velocity based on the pulse wave signal of each measurement site detected by the pulse wave detection unit 216, and outputs the result to the health state estimation unit 222 and the output unit 224. Specifically, for example, as illustrated in FIG. 13, the PWV calculation unit 220 calculates a time difference (pulse wave propagation time) T [seconds] at a reference point (such as a rising point) of the pulse wave signal of each measurement site detected by the pulse wave detection unit 216, and assuming that L[m] is a difference in distance from the heart between each measurement site, can calculate the pulse wave velocity V [m/second] by the following expression (1).

$$V = L/T \qquad (1)$$

Note that the pulse wave velocity V may be calculated simultaneously with the pulse wave signal of each measurement site detected by the pulse wave detection unit 216.

Note that the pulse wave propagation time T [seconds] can also be calculated by the following expression (2).

$$T = (C/360) \times (\tan^{-1}(H(y)/y) - \tan^{-1}(H(x)/x)) \quad (2)$$

where x and y are pulse wave signals in two measurement sites, H(x) and H(y) are Hilbert transforms of each other, and C [seconds] is a frequency of the pulse wave signal x or y, or an average of both.

Note that a plurality of patterns are previously stored in a memory (unillustrated) for each combination of measurement sites, the distance L may be determined according to the subject (measurement site) detected by the subject detection unit 116. For example, when the user inputs body type information such as age, gender, height, and weight, the distance L most fit to the body type information may be determined.

The health state estimation unit 222 estimates the health state of the human body imaged by the imaging device 100 based on the pulse rate calculated by the pulse rate calculation unit 218 and the pulse wave velocity calculated by the PWV calculation unit 220. The health state estimation unit 222 includes a blood pressure estimation unit 228 for estimating blood pressure, an arteriosclerosis state estimation unit 230 for estimating an arteriosclerosis state, and an autonomic nervous activity state 232 for estimating an autonomic nervous activity state. The health state estimation unit 222 outputs the estimation results to the output unit 224.

The output unit 224 outputs various information (such as pulse rate, pulse velocity, blood pressure, arteriosclerosis state, and autonomic nervous activity state) calculated by the calculation unit 212, for example, to the display unit 206, the storage unit 204, and the like.

Note that the present embodiment may be configured such that the PWV calculation unit 220 outputs a pulse wave propagation time T to the health state estimation unit 222 and the health state estimation unit 222 estimates the health state of the human body using the pulse wave propagation time T.

More specifically, the health state estimation unit 222 can calculate a difference R (that is, $R = |T_2 - T_1|$) between a pulse wave propagation time $T_1$ before a stimulus is applied to the human body and a pulse wave propagation time $T_2$ after the stimulus is applied to the human body and can estimate the mental and physical state of the human body from the difference R. The state of a healthy person changes greatly, but the state of an unhealthy person changes slightly. The following is considered as the stimulus applied to a living body.

Figure 14:
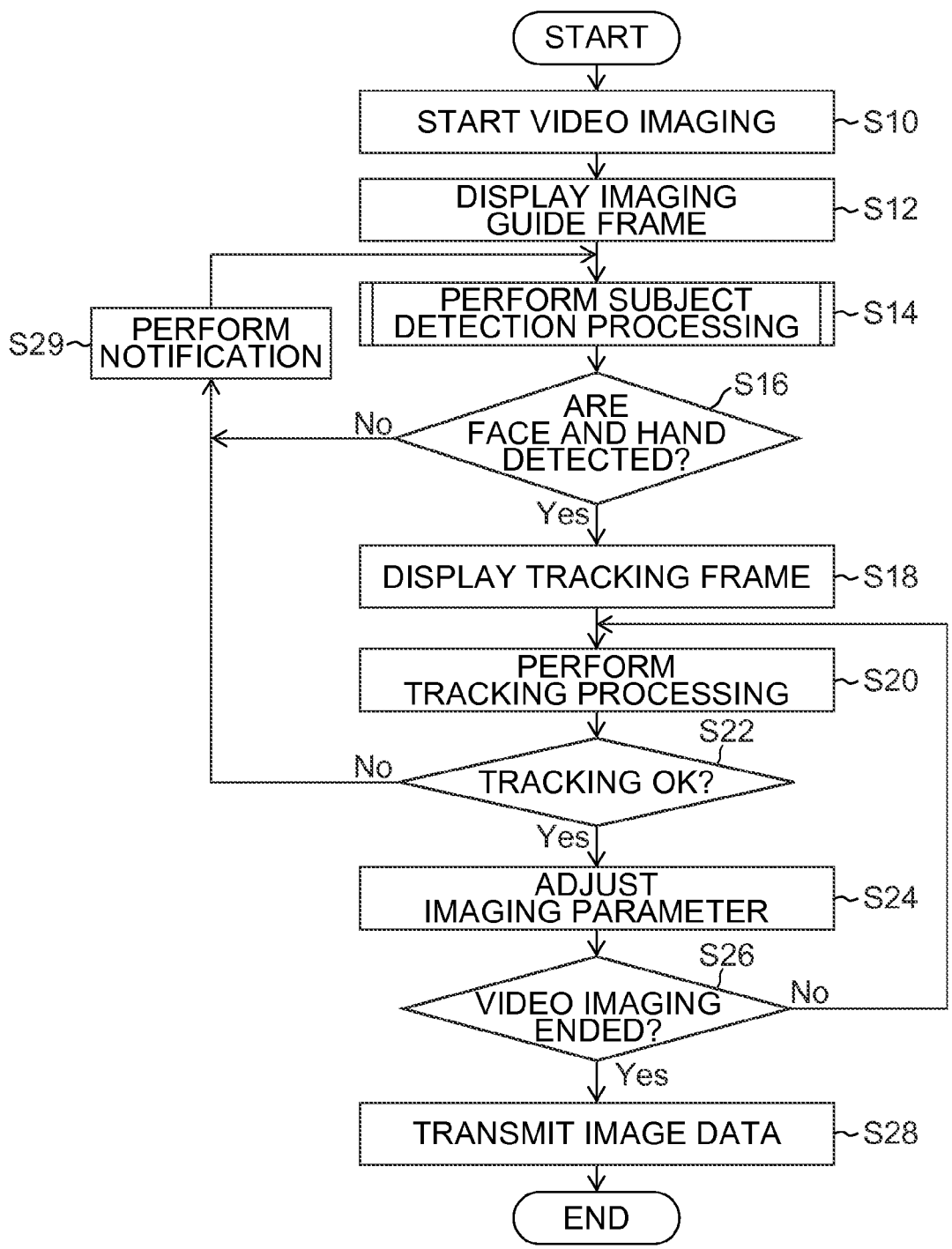
FIG. 14 is a flowchart illustrating processing to be performed by the imaging device according to the first embodiment.

Stimulus for the senses: flash, good smell, loud sound, vinegar in the mouth, and the like Mental stimulus: is spoken, video is shown, music is heard, and the like Stimulus to muscle: run, stand up, lift a heavy object, and the like Now, the description focuses on processing to be performed in the first embodiment. FIG. 14 is a flowchart illustrating processing to be performed by the imaging device 100 according to the first embodiment.

Figure 15:
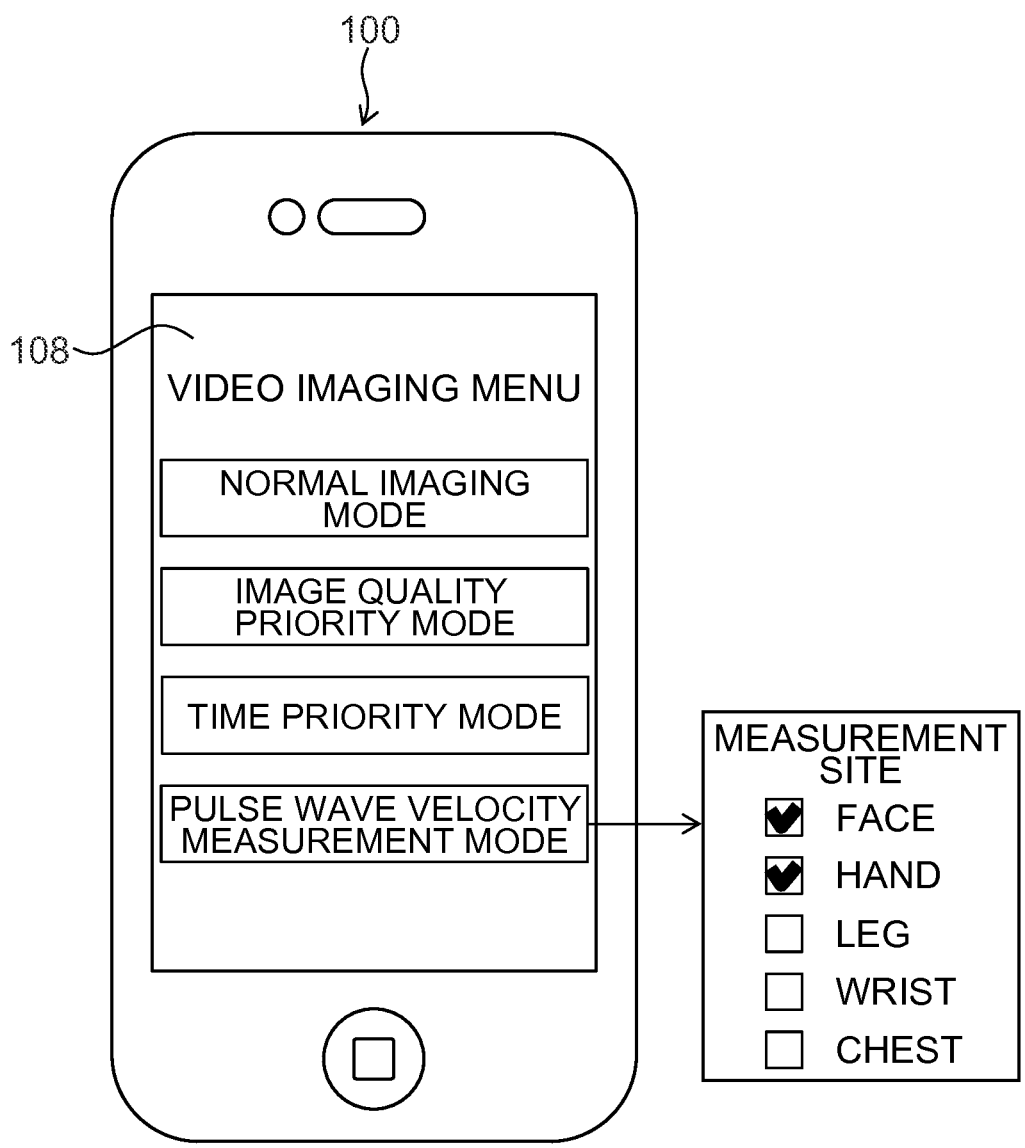
FIG. 15 is a view of an operation screen for starting video imaging.

First, as an "imaging step" of the present invention, video imaging starts (step S10). More specifically, as illustrated in FIG. 15, in a state in which "video imaging menu" is displayed on a screen of the display unit 108 of the imaging device 100, when the user selects "pulse wave velocity measurement mode", the control unit 104 controls the imaging unit 102 to start video imaging. In addition, the "pulse wave velocity measurement mode" includes a submenu on which a measurement site can be selected as an operation option. The face and hand are selected as the default measurement sites (first and second measurement sites). When the measurement site is changed, the measurement site can be changed to a desired measurement site by opening the submenu and selecting or deselecting a check box corresponding to the desired measurement site. Note that when the user captures an image of himself or herself, an in-camera function of the imaging device 100 is used.

When the video imaging starts in this manner, the imaging support unit 119 displays an imaging guide frame on the screen of the display unit 108 (step S12). For example, as illustrated in FIGS. 3 and 4, the face guide frame 140 and the hand guide frame 142 are displayed on the screen of the display unit 108. Thus when the imaging guide frames corresponding to the respective measurement sites are displayed on the screen of the display unit 108, for example, as illustrated in FIG. 5, the user tends to capture an image of the face and the hand at a position and with a size corresponding to the face guide frame 140 and the hand guide frame 142 respectively. This makes it easy to determine the position and the size of each measurement site, and hence can reduce the time required to perform measurement site detection processing and tracking processing and enables measurement to be made in a stable manner and with high accuracy.

Then, subject detection processing as a "subject detection step" of the present invention is performed (step S14). Specifically, the subject detection unit 116 detects two different parts (first and second measurement sites) of the human body as the particular subject regions, for example, in the first inputted frame image (initial frame image) of the image data acquired by the imaging unit 102.

Figure 16:
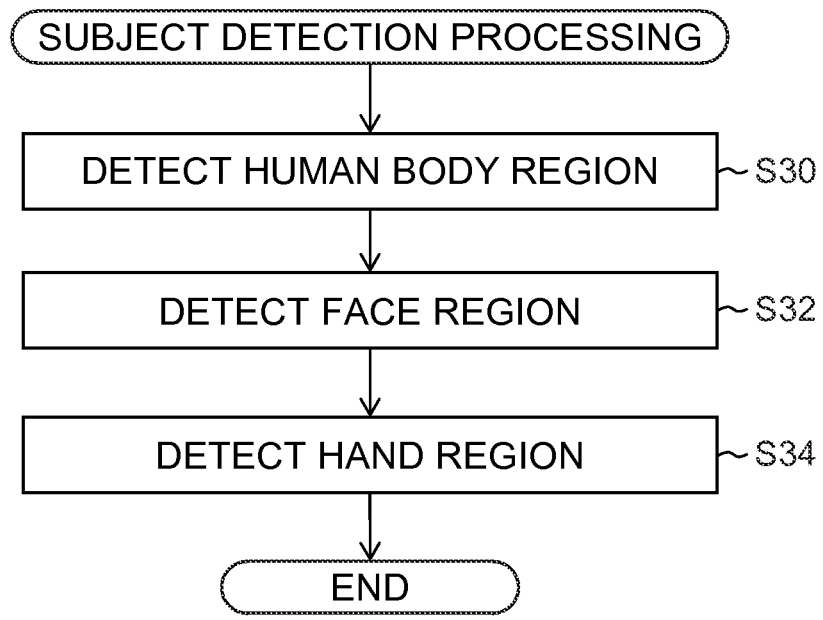
FIG. 16 is a flowchart illustrating subject detection processing.

FIG. 16 is a flowchart illustrating the subject detection processing. First, the human body region detection unit 120 of the subject detection unit 116 detects a human body region of the subject (step S30). Then, the face region detection unit 122 detects a face region (step S32). Further, the cheek region detection unit 126 and the forehead region detection unit 128 detect a cheek region and a forehead region respectively. Then, the hand region detection unit 124 detects a hand region (step S34). Further, the palm region detection unit 130 and the hand finger region detection unit 132 detect a palm region and a hand finger region respectively. Then, the subject detection processing ends.

Referring back to FIG. 14, the subject detection unit 116 determines whether or not the cheek region and the palm region are detected (step S16). If the determination in step S14 is affirmative, the tracking processing unit 118 sets the cheek region and the palm region as the respective tracking regions, and displays the tracking frames 154 and 156 in respective tracking regions on the screen of the display unit 108 as illustrated in FIG. 5 (step S18). Note that the tracking frames 154 and 156 are the same as the subject frames 150 and 152 except for the display color. Then, the tracking processing unit 118 performs tracking processing on these tracking regions as the "tracking processing step" of the present invention (step S20). In the tracking processing, a current frame image is searched for a region (corresponding to a tracking region in an original frame image) having a highest degree of similarity between the feature quantity of an image in a tracking region in a previous frame image and the feature quantity of an image in a tracking candidate region of the current frame image.

Then, the tracking processing unit 118 determines whether or not the tracking processing is performed normally (that is, determines whether or not the current frame image is searched for a region having a high degree of similarity to a tracking region in the previous frame image, and determines whether or not the positional relation with parallel performed region detection processing results is maintained) (step S22). If the determination in step S22 is affirmative, the tracking processing unit 118 adjusts various imaging parameters (focus, brightness, and the like) so as to be best suited for imaging the tracking regions through the control unit 104 (step S24).

Meanwhile, if the determination in step S16 or step S22 is negative, which means the region detection processing or the tracking processing is not performed appropriately, a notification message prompting the user to re-image the subject again is displayed on the screen of the display unit 108 as a "notification step" of the present invention (step S29). Then, the process returns to step S14, where the processes following the region detection processing are performed again. Note that the control unit 104 and the display unit 108 correspond to a "notification unit" of the present invention.

After step S24 is performed, a determination is made as to whether or not a video imaging end instruction is made (step S26). If the determination in step S26 is negative, the process returns to step S20, where the processes following the subject tracking processing are repeated. Meanwhile, if the determination in step S26 is affirmative, the video imaging ends under the control of the control unit 104 (step S26). Then, when an image data transmission instruction is made by operating the operation unit 110, the image data is transmitted to the PWV calculation device 200 via a network (step S28), and then the entire processing ends.

Figure 17:
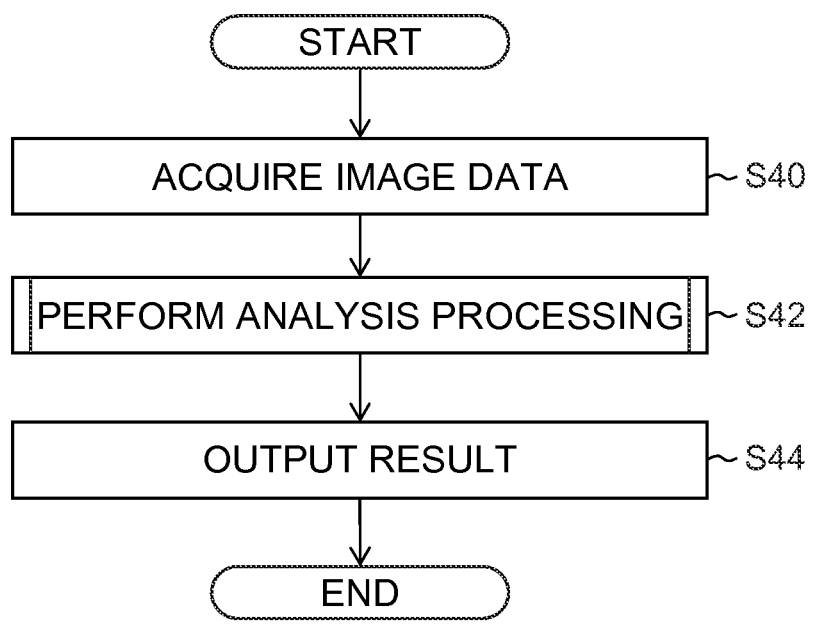
FIG. 17 is a flowchart illustrating processing to be performed by the pulse wave velocity calculation device according to the first embodiment.

FIG. 17 is a flowchart illustrating processing to be performed by the PWV calculation device 200 according to the first embodiment.

As illustrated in FIG. 17, the PWV calculation device 200 acquires the image data transmitted from the imaging device 100 (step S40). The image data acquired by the PWV calculation device 200 is temporarily stored in the storage unit 204.

Then, the calculation unit 212 reads the image data stored in the storage unit 204 and performs analysis processing for calculating the pulse wave velocity (step S42).

Then, the calculation unit 212 outputs the results (pulse rate, pulse velocity, blood pressure, arteriosclerosis state, and autonomic nervous activity state) obtained by the analysis processing (step S44).

Figure 18:
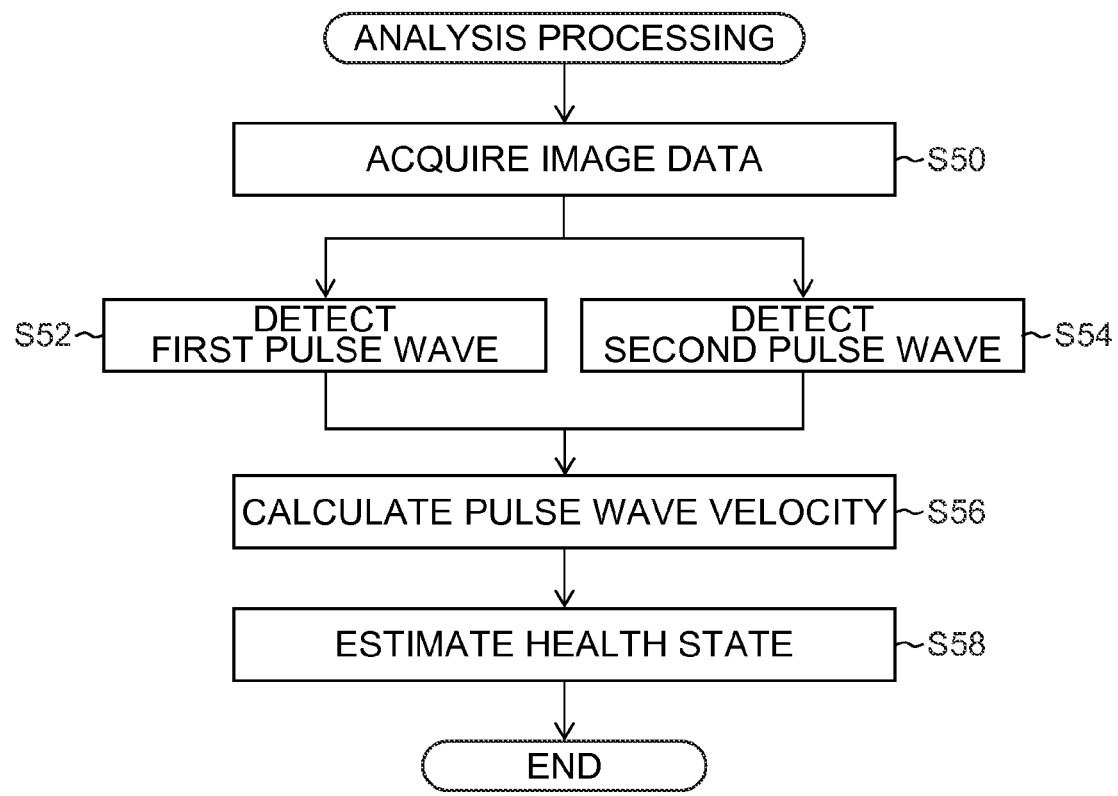
FIG. 18 is a flowchart illustrating image analysis processing.

Here, the description focuses on the analysis processing to be performed by the calculation unit 212. FIG. 18 is a flowchart illustrating image analysis processing.

First, the pulse wave detection unit 216 acquires the image data stored in the storage unit 204 (step S50). Note that the pulse wave detection unit 216 may acquire the image data directly from the imaging device 100.

Then, as a "pulse wave detection step" of the present invention, the pulse wave detection unit 216 detects a change in pixel value in the cheek region and the palm region, which are two different parts (first and second measurement sites respectively) of the human body, based on the image data outputted from the imaging device 100, thereby to acquire the pulse wave signal (pulse wave data) of the respective measurement sites (steps S52 and S54).

Then, as a "pulse wave velocity calculation step" of the present invention, the pulse wave velocity calculation unit 220 calculates the pulse wave velocity from a time difference of the pulse wave signal of each measurement site (step S56).

Then, as a "health state estimation step" of the present invention, the health state estimation unit 222 estimates the blood pressure, the arteriosclerosis state, and the autonomic nervous activity state as the health state of the human body imaged by the imaging device 100, based on the pulse wave velocity calculated by the pulse wave velocity calculation unit 220 (step S58).

Figure 19:
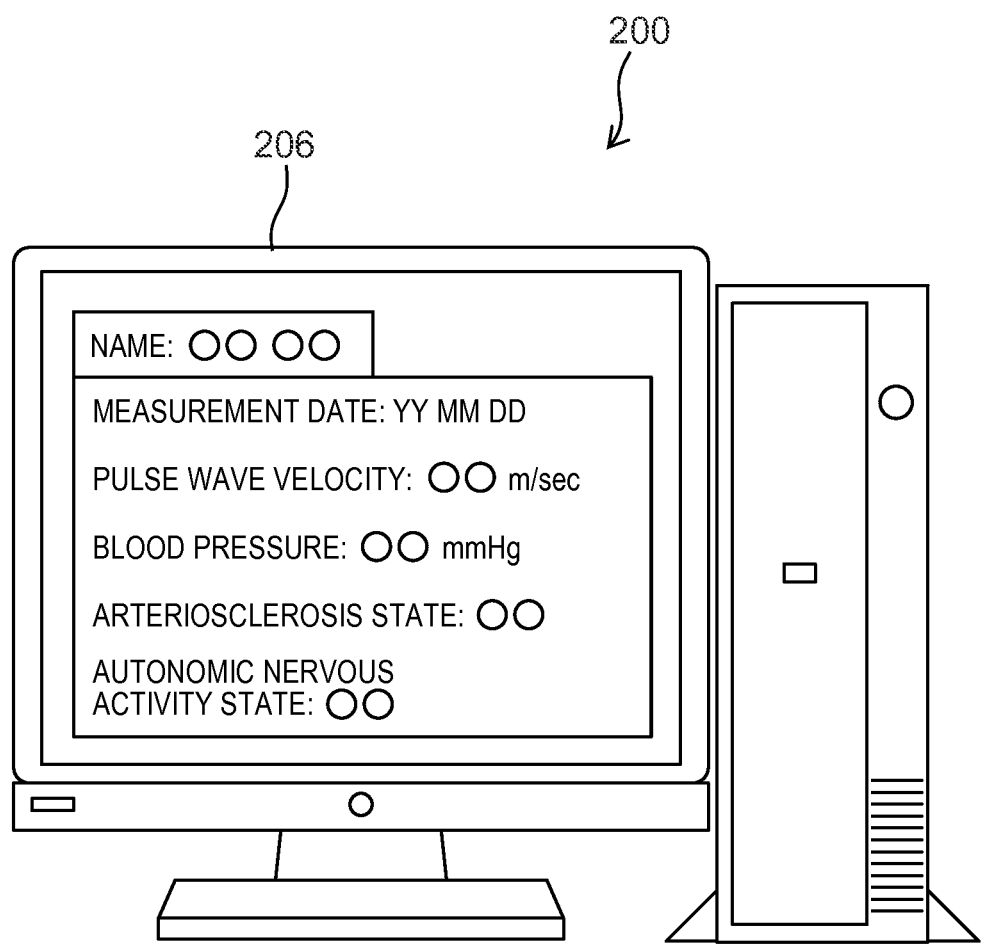
FIG. 19 is a view illustrating a state in which measurement results are displayed on a screen of a display unit of the pulse wave velocity calculation device.
Figure 20:
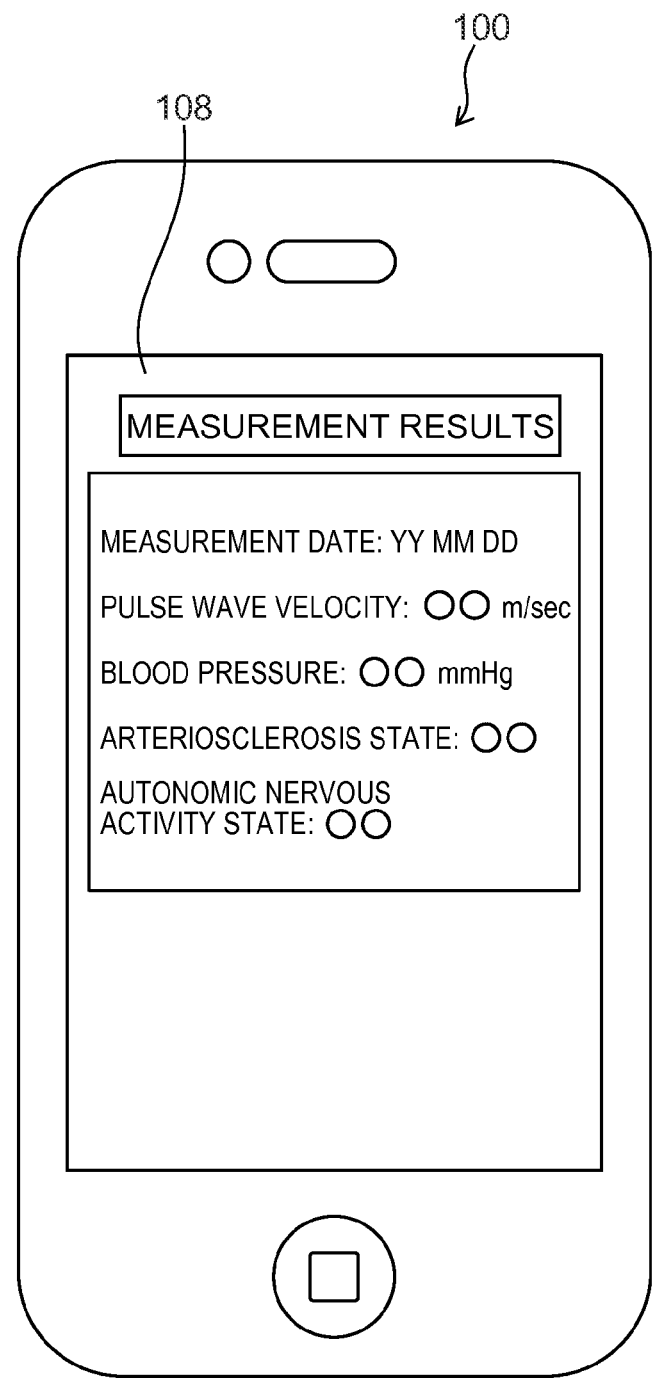
FIG. 20 is a view illustrating a state in which measurement results are displayed on a screen of the display unit of the imaging device.

Thus obtained various information (pulse wave velocity, blood pressure, arteriosclerosis state, and autonomic nervous activity state) is displayed on a screen of the display unit 206 of the PWV calculation device 200, for example, as illustrated in FIG. 19. Thus, in a hospital or the like where the PWV calculation device 200 is installed, the physician can easily grasp the health state of the user at a remote place without directly facing the user (patient, etc.,) imaged by the imaging device 100 by confirming the various information displayed on the screen of the display unit 206. In addition, the physician can grasp a change in physical condition of the user at an early stage and hence can prevent disease. Meanwhile, the user can measure his or her health state in a simple manner and can improve convenience. Note that as illustrated in FIG. 20, the pulse wave velocity, the blood pressure, the arteriosclerosis state, and the autonomic nervous activity state may be displayed on the screen of the display unit 108 of the imaging device 100. This makes it possible for the user of the imaging device 100 to grasp his or her own health state on a daily basis.

As described above, the present embodiment can obtain the pulse wave velocity based on the image data obtained by simultaneously imaging two different parts (first and second measurement sites) of a human body in a non-contact state by a single visible light camera, and hence can be used for everyday use by general users at low cost without being affected by posture or the like and can improve measurement accuracy in the pulse wave velocity. In addition, the present embodiment allows the image data to be imaged in a non-contact state in each measurement site, and thus can obtain the pulse wave velocity in a stable manner and with high accuracy without being affected by external pressure unlike a case of mounting the pulse wave sensor.

Note that according to the present embodiment, the PWV calculation device 200 performs the pulse wave velocity calculation processing and the health state estimation processing, but, without being limited to this, the imaging device 100 may perform these processes. This embodiment can calculate the pulse wave velocity and the like in real time while imaging two different parts of a human body, and hence the user of the imaging device 100 can easily grasp his or her own health state.

Second Embodiment

Now, the description focuses on a second embodiment of the present invention. Note that the description of the components common to the first embodiment is omitted and the following description will mainly focus on the characteristic components of the present embodiment.

Figure 21:
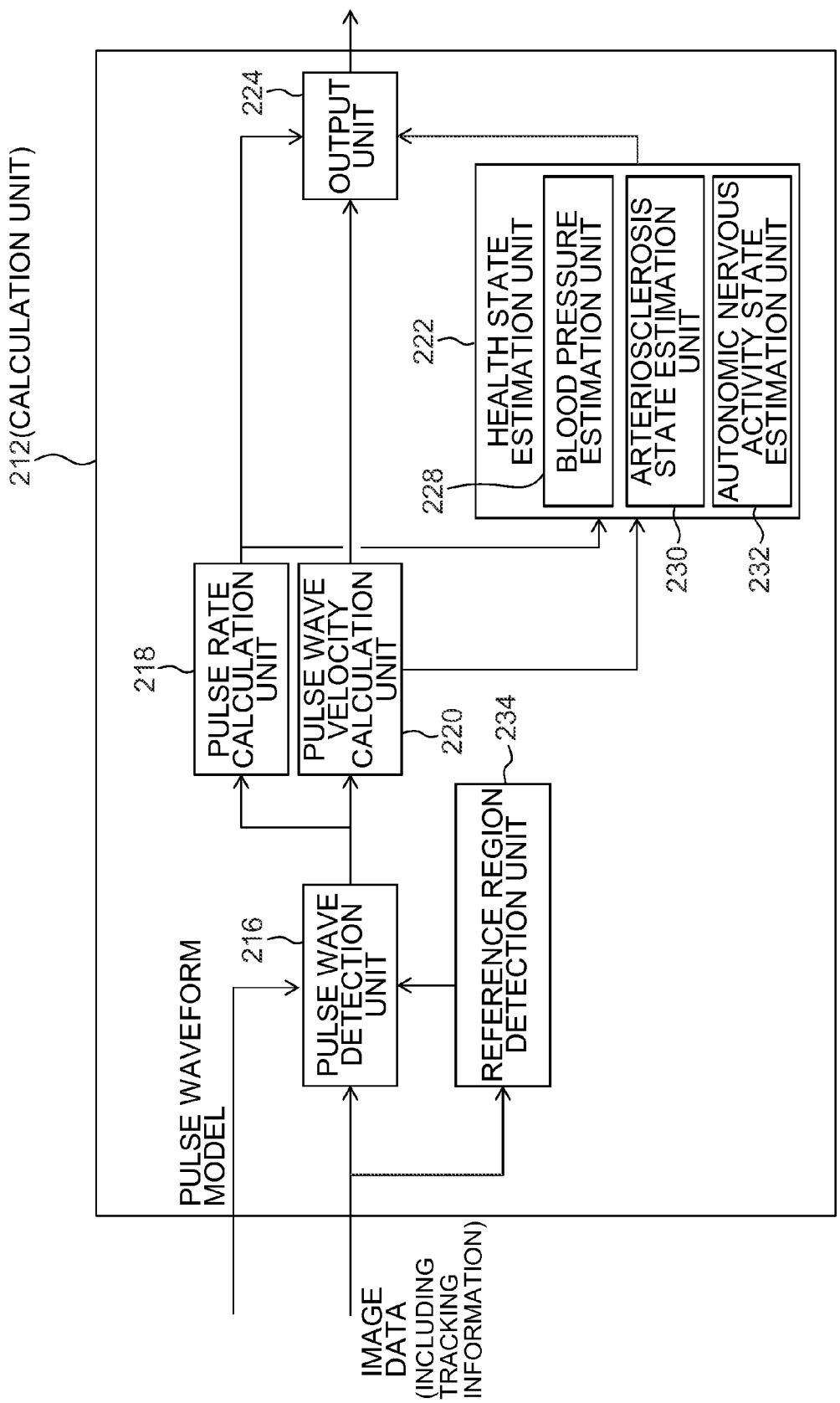
FIG. 21 is a block diagram illustrating a configuration of the calculation unit of the pulse wave velocity calculation device according to a second embodiment.

FIG. 21 is a block diagram illustrating a configuration of the calculation unit 212 of the PWV calculation device 200 according to the second embodiment. It should be noted that in FIG. 21, the same reference numbers are assigned to the components common to FIG. 8, and the description thereof is omitted.

According to the second embodiment, the calculation unit 212 includes a reference region detection unit 234 which detects a temporal variation (color change in skin) of a pixel value in a reference region in order to detect the light amount of illumination light or a temporal variation in color from each frame image. Note that the reference region detection unit 234 is a processing unit for performing an "optical information detection step" of the present invention. The following description focuses on a case in which the light amount of illumination light changes with time as an example, but the same description applies to a case in which the color of illumination light changes with time.

The reference region is a region for detecting a temporal variation in light amount of illumination light. Therefore, the pixel value is not changed by pulsation (blood flow), and hence the reference region needs to be a site in which an illumination variation can be observed in the same manner as in a body surface of the human body to be measured. In addition, it is preferable that the reference region has a small regional variation and is a somewhat large region. In light of these, a region other than the skin is preferable as the reference region, and for example, clothing, glasses, whites of the eyes, teeth, a reference seal, and the like are considered. Of them, the whites of the eyes are more preferable in that the brightness of illumination light and the temporal variation in color can be detected in a stable and reliable manner without being affected by the state of the user. Note that the pixel value of each pixel in the reference region contains various noise components like the above described measurement sites, and hence it is preferable to perform filtering processing and outlier processing using various filters (a moving average filter, a median filter, and a spatial frequency filter), which allows the temporal variation in light amount of illumination light to be detected without being affected by noise.

The results (that is, a change in pixel value in the reference region) detected by the reference region detection unit 234 are outputted to the pulse wave detection unit 216.

As a "correction step" of the present invention, the pulse wave detection unit 216 corrects the pixel value in each measurement site based on the change in pixel value in the reference region detected by the reference region detection unit 234. Specifically, the pixel value in each measurement site changes in proportion to a variation in light amount of illumination light, and hence a correction is performed by dividing the pixel value (measured value) in each measurement site by the ratio of the variation amount of the light amount.

For example, as illustrated in FIG. 22, assuming that A is a reference pixel value (such as a time average pixel value) in the reference region, B is a pixel value in the reference region when the light amount changes, and C is a pixel value in the measurement site (first or second measurement sites) at that time, a corrected pixel value X in the measurement site can be calculated by the following expression (3).

$$X = A \times C / B \quad (3)$$

As a "pulse wave detection step" of the present invention, the pulse wave detection unit 216 uses the corrected pixel value X instead of the pixel value C before correction to detect the pulse wave. This makes it possible to detect the pulse wave in a stable and reliable manner without being affected by the light amount of illumination light or the temporal variation in color and hence to calculate the pulse wave velocity with a good accuracy.

Hereinbefore, the pulse wave velocity measurement method and system as well as the imaging device according to the present invention have been described in detail, but the present invention is not limited to the above embodiments and it will be apparent that various improvements and modifications can be made to the present invention without departing from the spirit and scope of the present invention.

What is claimed is:

1. A pulse wave velocity measurement method comprising:
   an imaging step of simultaneously imaging mutually different two parts from among plural parts of a user's human body in a non-contact state by a single visible light camera and generating continuous time series image data, said single visible light camera being configured for everyday use by the user;
   a pulse wave detection step of detecting each pulse wave in the different two parts of the human body from the image data based on a temporal change in pixel value of the different two parts of the human body; and
   a pulse wave velocity calculation step of calculating a pulse wave velocity of the human body based on a time difference between pulse waves in the different two parts of the human body.

2. The pulse wave velocity measurement method according to claim 1, further comprising a subject detection step of detecting the different two parts of the human body from an image imaged by the imaging step.

3. The pulse wave velocity measurement method according to claim 2, further comprising a notification step of notifying a re-imaging of the different two parts of the human body if the different two parts of the human body cannot be detected from the image by the subject detection step.

4. The pulse wave velocity measurement method according to claim 1, comprising a tracking processing step of performing tracking processing on the different two parts of the human body by setting a region containing the different two parts of the human body in a first image of a plurality of images constituting the image data as a tracking region, extracting a feature quantity from an image in the tracking region, and detecting an image region having the highest degree of similarity to the feature quantity in a second image chronologically following the first image as a region containing the different two parts of the human body.

5. The pulse wave velocity measurement method according to claim 1, wherein the different two parts of the human body are a face and a hand.

6. The pulse wave velocity measurement method according to claim 1, wherein said single visible light camera comprises an imaging lens and a visible light image element that receives visible light to capture a subject image through the imaging lens and convert the subject image to color image data.

7. A pulse wave velocity measurement method comprising:
   an imaging step of simultaneously imaging different two parts from among plural parts of a human body in a non-contact state by a single visible light camera and generating continuous time series image data;
   an optical information detection step of detecting temporal variation information about at least one of a light amount and a color of illumination light emitted to the different two parts of the human body from the image data based on a temporal change in pixel value at a reference region other than the different two parts of the human body;
   a correction step of correcting the image data so as to cancel an effect due to the temporal variation in the light amount or the color of the illumination light based on the variation information detected by the optical information detection step;

a pulse wave detection step of detecting each pulse wave in the different two parts of the human body from the image data corrected by the correction step based on the temporal change in pixel value of the different two parts of the human body; and a pulse wave velocity calculation step of calculating a pulse wave velocity of the human body based on a time difference between pulse waves in the different two parts of the human body.

8. The pulse wave velocity measurement method according to claim 7, wherein the reference region is a region other than a skin of the human body.

9. The pulse wave velocity measurement method according to claim 8, wherein the reference region is whites of the eyes of the human body.

10. The pulse wave velocity measurement method according to claim 7, wherein said single visible light camera comprises an imaging lens and a visible light image element that receives visible light to capture a subject image through the imaging lens and convert the subject image color image data.

11. A pulse wave velocity measurement method comprising:

an imaging step of simultaneously imaging different two parts from among plural parts of a user's human body in a non-contact state by a single visible light camera and generating continuous time series image data, said single visible light camera being configured for everyday use by the user;

an interpolation step of generating interpolation data obtained by temporally interpolating a temporal change in pixel value of the different two parts of the human body from the image data;

a pulse wave detection step of detecting each pulse wave in the different two parts of the human body based on the interpolation data; and a pulse wave velocity calculation step of calculating a pulse wave velocity of the human body based on a time difference between pulse waves in the different two parts of the human body.

12. The pulse wave velocity measurement method according to claim 11, wherein the interpolation step selects a waveform model most fit to the temporal change in pixel value of the different two parts of the human body from a plurality of waveform models prepared in advance, and generates the interpolation data based on the selected waveform model.

13. The pulse wave velocity measurement method according to claim 11, further comprising a health state estimation step of estimating a blood pressure, an arteriosclerosis state, or an autonomic nervous activity state based on the pulse wave velocity calculated by the pulse wave velocity calculation step.

14. The pulse wave velocity measurement method according to claim 11, wherein said single visible light camera comprises an imaging lens and a visible light image element that receives visible light to capture a subject image through the imaging lens and convert the subject image to color image data.

15. An imaging device comprising:

an imaging unit that simultaneously images mutually different two parts from among plural parts of a user's human body in a non-contact state by a single visible light camera and generates continuous time series image data, said single visible light camera being configured for everyday use by the user;

a control unit; and a guide frame display unit that is controlled by said control unit to display an imaging guide frame corresponding to the mutually different two parts of the human body on a screen that is simultaneously displaying the image imaged by the imaging unit, thereby visually indicating whether the mutually different two parts are being properly imaged by said single visible light camera.

16. The imaging device according to claim 15, further comprising an operation unit that allows a user to set the mutually different two parts from among the plural parts of the human body.

17. The imaging device according to claim 15, wherein said single visible light camera comprises an imaging lens and a visible light image element that receives visible light to capture a subject image through the imaging lens and convert the subject image to color image data.

* * * * *